(12) United States Patent
Lee

(10) Patent No.: US 10,417,513 B2
(45) Date of Patent: Sep. 17, 2019

(54) PHOTOSENSITIVE THIN FILM DEVICE AND BIOMETRIC INFORMATION SENSING APPARATUS INCLUDING THE PHOTOSENSITIVE THIN FILM DEVICE

(71) Applicant: Samsung Display Co., Ltd., Yongin-si, Gyeonggi-do (KR)

(72) Inventor: Taehee Lee, Yongin-si (KR)

(73) Assignee: Samsung Display Co., Ltd., Yongin-si (KR)

(*) Notice: Subject to any disclaimer, the term of this patent is extended or adjusted under 35 U.S.C. 154(b) by 152 days.

(21) Appl. No.: 15/250,639

(22) Filed: Aug. 29, 2016

(65) Prior Publication Data
US 2017/0249520 A1 Aug. 31, 2017

(30) Foreign Application Priority Data
Feb. 26, 2016 (KR) .................. 10-2016-0023625

(51) Int. Cl.
*H01L 27/146* (2006.01)
*G06K 9/00* (2006.01)
(Continued)

(52) U.S. Cl.
CPC .......... *G06K 9/00892* (2013.01); *A61B 5/117* (2013.01); *A61B 5/489* (2013.01); *A61B 5/6817* (2013.01); *G06K 9/0004* (2013.01); *G06K 9/209* (2013.01); *G06K 9/2018* (2013.01); *H01L 27/1461* (2013.01); *H01L 27/14616* (2013.01); *H01L 27/14623* (2013.01); *H01L 27/14645* (2013.01); *H01L 27/14678* (2013.01); *H01L 31/02164* (2013.01);
(Continued)

(58) Field of Classification Search
CPC ......... H01L 31/0512; H01L 31/022416; H01L 29/78696; H01L 27/124; H01L 27/14603; H01L 27/14614
See application file for complete search history.

(56) References Cited

U.S. PATENT DOCUMENTS 3,459,944 A 8/1969 Triebwasser
6,504,176 B2 1/2003 Kitabatake et al.
(Continued)

FOREIGN PATENT DOCUMENTS

JP 2011-147469 A 8/2011
KR 10-2006-0002448 A 1/2006
(Continued)

*Primary Examiner* — Joseph M Galvin, III
(74) *Attorney, Agent, or Firm* — Lewis Roca Rothgerber Christie LLP

(57) ABSTRACT

A photosensitive thin film device includes a substrate that is transparent and insulative; a first electrode on the substrate; a circular semiconductor layer on the substrate and surrounding a perimeter of the first electrode; a circular second electrode on the substrate and surrounding a perimeter of the semiconductor layer; an interlayer insulating layer on the semiconductor layer and the first and second electrodes and having a first aperture exposing the first electrode; and a conductive layer including an upper surface light barrier arranged on the interlayer insulating layer and covering an upper surface of the semiconductor layer, and a contact plug extending from the upper surface light barrier and connected to the first electrode via the first aperture.

20 Claims, 22 Drawing Sheets

(51) Int. Cl.
    *H01L 31/0224*     (2006.01)
    *H01L 31/0216*     (2014.01)
    *A61B 5/00*     (2006.01)
    *A61B 5/117*     (2016.01)
    *G06K 9/20*     (2006.01)
    *H02S 40/44*     (2014.01)

(52) U.S. Cl.
    CPC ...... *H01L 31/022416* (2013.01); *H02S 40/44* (2014.12); *A61B 2562/0209* (2013.01); *A61B 2562/0233* (2013.01); *A61B 2562/0238* (2013.01); *A61B 2562/06* (2013.01); *G06K 2009/00932* (2013.01)

(56) References Cited

U.S. PATENT DOCUMENTS

| | | | |
|---|---|---|---|
| 9,236,438 B2 * | 1/2016 | Lin | H01L 29/4238 |
| 2005/0270454 A1 * | 12/2005 | Ahn | G02F 1/133555 |
| | | | 349/114 |
| 2005/0285108 A1 | 12/2005 | Choi | |
| 2008/0179665 A1 * | 7/2008 | Lee | H01L 27/108 |
| | | | 257/330 |
| 2009/0209836 A1 | 8/2009 | Niwayama | |
| 2013/0207101 A1 * | 8/2013 | Yamazaki | H01L 29/41733 |
| | | | 257/43 |
| 2014/0024905 A1 | 1/2014 | Sarrafzadeh et al. | |
| 2014/0110810 A1 * | 4/2014 | Yamamoto | H01L 27/1443 |
| | | | 257/443 |
| 2014/0332692 A1 * | 11/2014 | Lutz | H01L 31/115 |
| | | | 250/371 |

FOREIGN PATENT DOCUMENTS

| | | |
|---|---|---|
| KR | 10-2006-0045089 A | 5/2006 |
| KR | 10-2009-0011030 A | 1/2009 |
| KR | 10-2011-0006032 A | 1/2011 |
| KR | 10-1044883 B1 | 6/2011 |
| KR | 10-2011-0078231 A | 7/2011 |
| KR | 10-1306659 B1 | 9/2013 |
| KR | 10-2014-0038931 A | 3/2014 |

* cited by examiner

PHOTOSENSITIVE THIN FILM DEVICE AND BIOMETRIC INFORMATION SENSING APPARATUS INCLUDING THE PHOTOSENSITIVE THIN FILM DEVICE

CROSS-REFERENCE TO RELATED PATENT APPLICATION

This application claims priority to and the benefit of Korean Patent Application No. 10-2016-0023625, filed on Feb. 26, 2016, in the Korean Intellectual Property Office, the disclosure of which is incorporated herein in its entirety by reference.

BACKGROUND

1. Field

One or more embodiments relate to photosensitive thin film devices and apparatuses including the same, and more particularly, to a biometric information sensing apparatus.

2. Description of the Related Art

Technologies that sense or detect biometric information are in demand. For example, in addition to a fingerprint or an iris, a vein pattern is also being used as authentication means. As the performance of portable devices, such as smartphones or wearable devices, improves, such portable devices may have, in addition to other functions, a function of measuring and sensing body information, such as a heart rate, oxygen saturation, and electrocardiogram in order to monitor the health state of users.

To measure such biometric information, a light-emitting device for radiating light to a body and a light-receiving device for receiving light reflected or transmitted through the body are used. A biometric information sensing apparatus may have a large area (or large size) when the light-receiving device receives light transmitted through the body because a portion of the body should be located between the light-emitting device and the light-receiving device. When the light-receiving device receives light reflected by the body, sensing accurate biometric information may be difficult due to noise and/or the like generated by light directly radiated to the light-receiving device.

SUMMARY

One or more embodiments include a lightweight and thin biometric information sensing apparatus capable of accurately sensing biometric information, and a photosensitive thin film device suitable for the biometric information sensing apparatus.

Additional aspects will be set forth in part in the description which follows and, in part, will be apparent from the description, or may be learned by practice of the presented embodiments.

According to one or more embodiments, a photosensitive thin film device includes a substrate that is transparent and insulative; a first electrode on the substrate; a semiconductor layer on the substrate and surrounding a perimeter of the first electrode; a second electrode on the substrate and surrounding a perimeter of the semiconductor layer; an interlayer insulating layer on the semiconductor layer and the first and second electrodes and having a first aperture exposing the first electrode; and a conductive layer including an upper surface light barrier arranged on the interlayer insulating layer and covering an upper surface of the semiconductor layer, and a contact plug extending from the upper surface light barrier and connected to the first electrode via the first aperture.

The semiconductor layer may have a ring-type planar shape having an inner edge and an outer edge. The first electrode may be arranged inside the inner edge and covers the inner edge. The second electrode may cover the outer edge.

The semiconductor layer may have a circular ring-type planar shape having a circular inner edge and a circular outer edge.

The semiconductor layer may include a first semiconductor layer on the substrate, and second semiconductor layers arranged between the first semiconductor layer and the first and second electrodes, the second semiconductor layers including heavily-doped impurities.

The interlayer insulating layer may have a second aperture spaced apart from the second electrode and surrounding a portion of a perimeter of the second electrode. The conductive layer may further include a lateral surface light barrier extending from the upper surface light barrier along the second aperture and covering a portion of a lateral surface of the semiconductor layer in a lateral direction.

The photosensitive thin film device may further include a connection line that extends from the second electrode in a lateral direction via a hole in the lateral surface light barrier on the substrate, the connection line being insulated from the lateral surface light barrier by the interlayer insulating layer.

The upper and lateral surface light barriers of the conductive layer may be configured to block light radiated from above the conductive layer toward the substrate from reaching the semiconductor layer.

As an amount of light radiated from below the substrate onto the semiconductor layer increases, a magnitude of a current flowing between the first and second electrodes via the semiconductor layer may increase.

According to one or more embodiments, a biometric information sensing apparatus includes a substrate that is transparent and insulative; a light sensor array including a plurality of pixels arranged in a matrix form on the substrate, each of the pixels including a photosensitive thin film device; and a light-emission unit arranged on the light sensor array and configured to emit light. The photosensitive thin film device may include a first semiconductor pattern of a ring type having an inner edge and an outer edge, the first semiconductor pattern being on the substrate; a first electrode arranged inside the inner edge on the substrate and connected to the first semiconductor pattern; a second electrode surrounding a perimeter of the first semiconductor pattern along the outer edge; an interlayer insulating layer arranged on the first semiconductor pattern and the first and second electrodes and having a first aperture exposing the first electrode; and a light barrier electrode including an upper surface light barrier arranged on the interlayer insulating layer and covering an upper surface of the first semiconductor pattern, and a contact plug extending from the upper surface light barrier and connected to the first electrode via the first aperture.

The light-emission unit may include at least one of a first light-emitting device configured to emit visible light of a first color, a second light-emitting device configured to emit visible light of a second color, and a third light-emitting device configured to emit near-infrared light.

Each of the plurality of pixels may include a thin film transistor, and the thin film transistor may include a second semiconductor pattern on the substrate, the second semiconductor pattern having first and second impurity regions and a channel region between the first and second impurity regions; a first gate electrode disposed between the substrate and the second semiconductor pattern such that at least a portion of the first gate electrode overlaps the channel region; a third electrode connected to the first impurity region; and a fourth electrode connected to the second impurity region and the second electrode of the photosensitive thin film device.

The thin film transistor may further include a second gate electrode connected to the first gate electrode via a contact plug that extends through the interlayer insulating layer, the second gate electrode being arranged on the interlayer insulating layer such that at least a portion of the second gate electrode overlaps the channel region.

The light sensor array may further include gate lines that electrically connect the first gate electrodes of the thin film transistors of pixels on a same row from among the plurality of pixels to one another; output lines that electrically connect the third electrodes of the thin film transistors of pixels on a same column from among the plurality of pixels to one another; and a bias line that electrically connects the light barrier electrodes of the photosensitive thin film devices of the plurality of pixels to one another.

The biometric information sensing apparatus may further include a power supply configured to apply a bias voltage to the bias line; and an image sensor controller configured to sequentially drive the gate lines, to receive sensing signals output from the plurality of pixels via the output lines, and to generate image data based on the sensing signals.

The light-emission unit may include a plurality of first light-emitting devices configured to emit red visible light, a plurality of second light-emitting devices configured to emit green visible light, and a plurality of third light-emitting devices configured to emit near-infrared light.

The biometric information sensing apparatus may further include a controller configured to control at least one of the first light-emitting devices, the second light-emitting devices, and the third light-emitting devices to emit light according to operation modes, receive image data from the image sensor controller, and analyze the image data according to the operation modes.

The controller may control the third light-emitting devices to emit light in a vein pattern sensing mode, control the second light-emitting devices to emit light in a pulse wave sensing mode or a heart rate measuring mode, and control the first light-emitting devices and the third light-emitting devices to alternately emit light in an oxygen saturation measuring mode.

The biometric information sensing apparatus may be a portable terminal having a wireless communication function.

The controller may authenticate a user by comparing a vein pattern of the user acquired by analyzing the image data in the vein pattern sensing mode with a pre-stored vein pattern.

The biometric information sensing apparatus may further include a transparent electrode arranged below the substrate; and earphones configured to be connected to the portable terminal and including first and second electrocardiogram sensing electrodes that respectively contact both ears of the user. The controller may measure an electrocardiogram of the user via the first and second electrocardiogram sensing electrodes and the transparent electrode.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
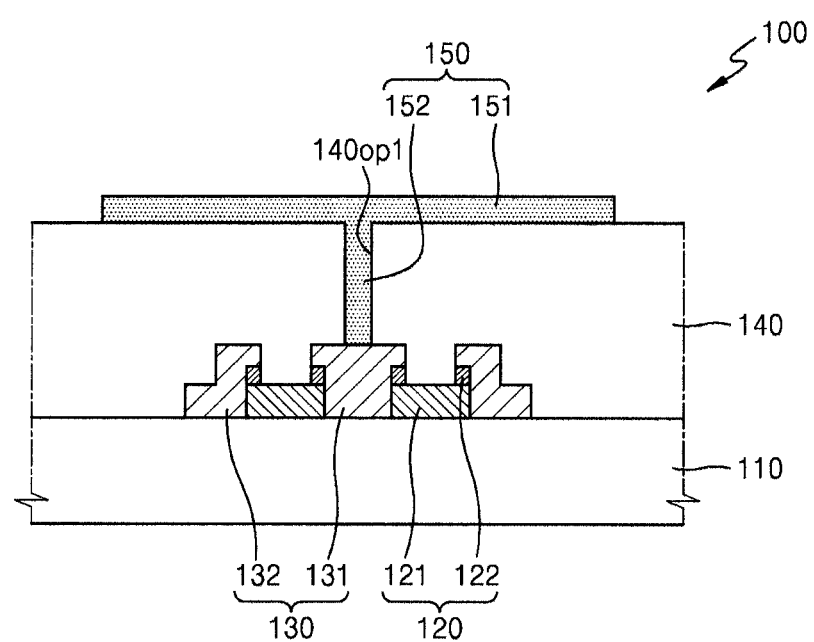
FIG. 1 is a cross-sectional view of a photosensitive thin film device according to an embodiment of the present invention.

Reference will now be made in detail to embodiments, examples of which are illustrated in the accompanying drawings, wherein like reference numerals refer to like elements (or components) throughout. In this regard, the present embodiments may have different forms and should not be construed as being limited to the descriptions set forth herein. Accordingly, the embodiments are merely described below, by referring to the figures, to explain aspects of the present description.

As used herein, the term "and/or" includes any and all combinations of one or more of the associated listed items. Expressions such as "at least one of," "one of," and "selected from," when preceding a list of elements, modify the entire list of elements and do not modify the individual elements of the list. Further, the use of "may" when describing embodiments of the present invention refers to "one or more embodiments of the present invention." Also, the term "exemplary" is intended to refer to an example or illustration.

As the invention allows for various changes and numerous embodiments, particular embodiments will be illustrated in the drawings and described in detail in the written description. Hereinafter, effects and features of embodiments of the present invention and a method for accomplishing them will be described more fully with reference to the accompanying drawings, in which embodiments of the invention are shown. This invention may, however, be embodied in many different forms and should not be construed as being limited to the embodiments set forth herein.

It will be understood that, although the terms "first," "second," "third," etc., may be used herein to describe various elements, components, regions, layers, and/or sections, these elements, components, regions, layers, and/or sections should not be limited by these terms. These terms are used to distinguish one element, component, region, layer, or section from another element, component, region, layer, or section. Thus, a first element, component, region, layer, or section discussed below could be termed a second element, component, region, layer, or section without departing from the spirit and scope of the present invention.

A relevant device or component (or relevant devices or components) according to embodiments of the present invention described herein may be implemented utilizing any suitable hardware (e.g., an application-specific integrated circuit), firmware (e.g., a DSP or FPGA), software, or a suitable combination of software, firmware, and hardware. For example, the various components of the relevant device(s) may be formed on one integrated circuit (IC) chip or on separate IC chips. Further, the various components of the relevant device(s) may be implemented on a flexible printed circuit film, a tape carrier package (TCP), a printed circuit board (PCB), or formed on a same substrate as one or more circuits and/or other devices. Further, the various components of the relevant device(s) may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the spirit and scope of the exemplary embodiments of the present invention.

Spatially relative terms, such as "top," "bottom," "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below," "beneath," or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

Further, it will also be understood that when one element, component, region, layer, and/or section is referred to as being "between" two elements, components, regions, layers, and/or sections, it can be the only element, component, region, layer, and/or section between the two elements, components, regions, layers, and/or sections, or one or more intervening elements, components, regions, layers, and/or sections may also be present.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "comprise," "comprises," "comprising," "includes," "including," and "include," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on," "connected to," "coupled to," "connected with," "coupled with," or "adjacent to" another element or layer, it can be "directly on," "directly connected to," "directly coupled to," "directly connected with," "directly coupled with," or "directly adjacent to" the other element or layer, or one or more intervening elements or layers may be present. Furthermore, "connection," "connected," etc., may also refer to "electrical connection," "electrically connected," etc., depending on the context in which such terms are used as would be understood by those skilled in the art. When an element or layer is referred to as being "directly on," "directly connected to," "directly coupled to," "directly connected with," "directly coupled with," or "immediately adjacent to" another element or layer, there are no intervening elements or layers present.

Sizes of elements (or components) in the drawings may be exaggerated for convenience of explanation. In other words, since sizes and thicknesses of components in the drawings are arbitrarily illustrated for convenience of explanation, the present invention is not limited thereto.

When a certain embodiment may be implemented differently, a specific process order may be performed differently from the described order. For example, two consecutively described processes may be performed substantially at the same time or performed in an order opposite to the described order.

One or more embodiments of the invention will be described below in more detail with reference to the accompanying drawings. Those components that are the same or are in correspondence may be given the same reference numeral regardless of the figure number, and redundant explanations may be omitted.

As used herein, "substantially," "about," and similar terms are used as terms of approximation and not as terms of degree, and are intended to account for the inherent deviations in measured or calculated values that would be recognized by those of ordinary skill in the art.

As used herein, the terms "use," "using," and "used" may be considered synonymous with the terms "utilize," "utilizing," and "utilized," respectively.

Features described in relation to one or more embodiments of the present invention are available for use in conjunction with features of other embodiments of the present invention. For example, features described in a first embodiment may be combined with features described in a second embodiment to form a third embodiment, even though the third embodiment may not be specifically described herein.

Also, any numerical range recited herein is intended to include all sub-ranges of the same numerical precision subsumed within the recited range. For example, a range of "1.0 to 10.0" or between "1.0 and 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such sub-ranges would comply with the requirements of 35 U.S.C. § 112, first paragraph, and 35 U.S.C. § 132(a).

Figure 2A:
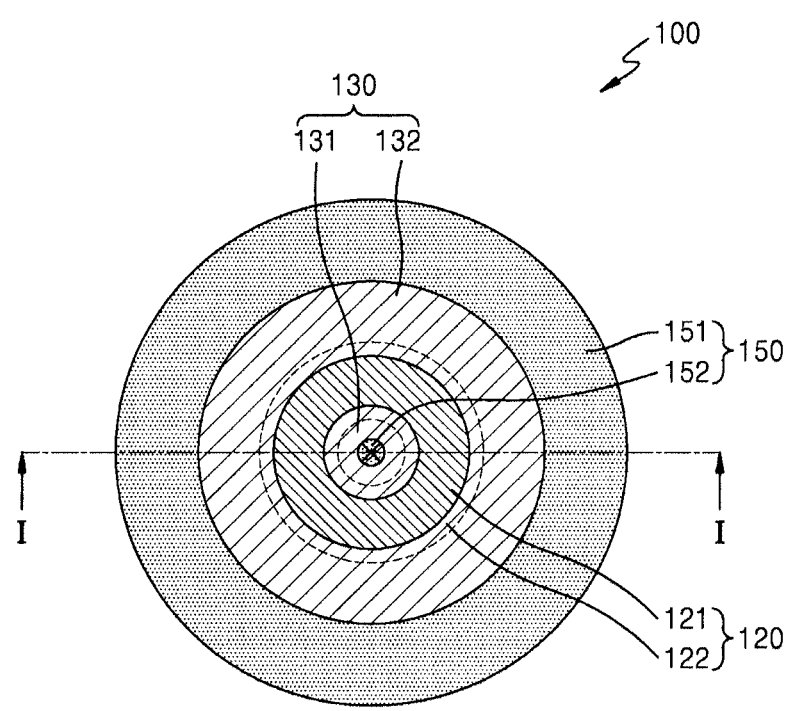
FIG. 2A is a plan view of the photosensitive thin film device according to the embodiment of FIG. 1.

FIG. 1 is a cross-sectional view of a photosensitive thin film device 100 according to an embodiment of the present invention and FIG. 2A is a plan view of the photosensitive thin film device 100 according to the embodiment of FIG. 1. FIG. 1 is a cross-sectional view taken along the line I-I of FIG. 2A.

Referring to FIGS. 1 and 2A, the photosensitive thin film device 100 may include a substrate 110, a semiconductor layer 120, a first electrode 131, a second electrode 132, an interlayer insulating layer 140, and a conductive layer 150. The substrate 110 may include a transparent insulative material. The first electrode 131 is disposed on the substrate 110, and the semiconductor layer 120 surrounds the perimeter (e.g., the circumference) of the first electrode 131. The second electrode 132 surrounds the perimeter (e.g., the circumference) of the semiconductor layer 120. The interlayer insulating layer 140 is disposed on the semiconductor layer 120 and the first and second electrodes 131 and 132, and has a first aperture 140op1 via which the first electrode 131 is exposed. The conductive layer 150 includes an upper surface light barrier unit 151 (e.g., an upper surface light barrier 151) disposed on the interlayer insulating layer 140 to cover an upper surface of the semiconductor layer 120, and a contact unit 152 (e.g., a contact plug 152) extending from the upper surface light barrier unit 151 and connected to the first electrode 131 via the first aperture 140op1.

For ease of understanding, FIG. 2A illustrates the conductive layer 150 positioned at the top and also illustrates planar shapes of the semiconductor layer 120 and the first and second electrodes 131 and 132 located below the conductive layer 150.

The substrate 110 may include a base substrate formed of any of various suitable transparent and insulative materials, such as glass or plastic. According to an embodiment, the substrate 110 may include a flexible base substrate. The flexible base substrate may be a substrate that may be easily bent, folded, and/or rolled. The flexible base substrate may be formed of ultra-thin glass or plastic. For example, the base substrate may include, but is not limited to, at least one plastic material including polyimide (PI), polyethyelene-terepthalate (PET), polyethyelenen napthalate (PEN), polycarbonate (PC), polyacrylate (PAR), polyetherimide (PEI), polyethersulphone (PES), polyphenylene sulfide (PPS), polyallylate, cellulose triacetate (TAC), cellulose acetate propionate (CAP), polydimethylsiloxane (PDMS), hexamethyldisiloxane (HMDSO), and/or combinations thereof.

The substrate 110 may further include a buffer layer on the base substrate. The buffer layer may prevent permeation of impure elements and may planarize the surface of the base substrate. A barrier layer may be interposed between the base substrate and the buffer layer of the substrate 110. When a buffer layer and/or a barrier layer, formed of an insulative material, are disposed on the base substrate, the base substrate may be formed of conductive metal or metal oxide. In this case, because the buffer layer and/or the barrier layer are insulative, the substrate 110 may be insulated from devices formed on the substrate 110.

The photosensitive thin film device 100 and/or a thin film transistor may be formed on the substrate 110, and unit pixels (e.g., pixels) each including the photosensitive thin film device 100 and the thin film transistor may be arranged in a matrix form.

The semiconductor layer 120 may be disposed on the substrate 110 and may have a ring-type planar shape. The semiconductor layer 120 may include a semiconductor material sensitive to visible light and/or infrared light, for example, amorphous silicon (a-Si) or amorphous silicon germanium (a-SiGe). According to another embodiment, the semiconductor layer 120 may include germanium (Ge), indium phosphide (InP), cadmium telluride (CdTe), and/or gallium arsenide (GaAs). According to another embodiment, the semiconductor layer 120 may include an organic semiconductor material and/or an oxide semiconductor material.

As shown in FIG. 2A, the semiconductor layer 120 may have a circular ring-type planar shape having a circular inner edge and a circular outer edge. However, the inner edge and the outer edge of the semiconductor layer 120 are not limited to a circular shape, and may have various suitable planar shapes, such as a polygon and an oval. For example, the semiconductor layer 120 may have a rectangular frame-type planar shape. Alternate planar shapes may be described below in more detail with reference to FIGS. 2B through 2D.

The semiconductor layer 120 may have a planar shape of a ring type including a straight portion and a curved portion. For example, at least one portion of the semiconductor layer 120 may have a shape such as an arc, and at least another portion thereof may have a straight line shape. For example, in a top view of the semiconductor layer 120, a left side and a right side thereof may have half arc shapes, and an upper side and a lower side thereof may have straight line shapes that connect the half arcs of the left and right sides to each other.

The first electrode 131 is disposed on the substrate 110 so as to be located inside the inner edge of the semiconductor layer 120. Accordingly, the semiconductor layer 120 surrounds the perimeter (e.g., the circumference) of the first electrode 131, and the first electrode 131 is electrically connected to the semiconductor layer 120. As illustrated in FIG. 1, the first electrode 131 may be disposed on the semiconductor layer 120 such that it covers the inner edge of the semiconductor layer 120. The first electrode 131 may directly contact the inner edge of the semiconductor layer 120. However, the inventive concept is not limited thereto, and the first electrode 131 may be disposed below the semiconductor layer 120, and a portion of the first electrode 131 may be covered by the semiconductor layer 120, and thus the inner edge of the semiconductor layer 120 may be located on the first electrode 131. As illustrated in FIG. 2A, the first electrode 131 may have a circular planar shape in correspondence with the shape of the inner edge of the semiconductor layer 120.

The second electrode 132 is disposed on the substrate 110 to surround the perimeter (e.g., the circumference) of the semiconductor layer 120, and is electrically connected to the semiconductor layer 120.

As illustrated in FIG. 1, the second electrode 132 may be formed on the semiconductor layer 120 such that it covers the outer edge of the semiconductor layer 120. The second electrode 132 may directly contact the outer edge of the semiconductor layer 120. However, the inventive concept is not limited thereto, and the second electrode 132 may be disposed below the semiconductor layer 120, and a portion of the second electrode 132 may be covered by the semiconductor layer 120, and thus the outer edge of the semiconductor layer 120 may be located on the second electrode 132.

As illustrated in FIG. 2A, the second electrode 132 may have a ring-type planar shape in correspondence with the shape of the outer edge of the semiconductor layer 120. For example, the second electrode 132 may have a circular ring-type planar shape or a quadrilateral-type planar shape. The second electrode 132 may linearly extend on the substrate 110 so as to be connected to another device, for example, the thin film transistor, on the substrate 110, The linear extension of the second electrode 132 may be referred to as a connection electrode or a connection line.

The first and second electrodes 131 and 132 may be portions of an electrode layer 130. The electrode layer 130 may be a single layer or multiple layers formed of a conductive material including molybdenum (Mo), aluminum (Al), copper (Cu), and/or titanium (Ti).

When the semiconductor layer 120 is irradiated with light, electrons within the semiconductor layer 120 are excited from a valence band to a conduction band. Accordingly, the semiconductor layer 120 becomes conductive, and the first electrode 131 and the second electrode 132 are electrically connected to each other. Depending on the amount of light radiated onto the semiconductor layer 120, resistance of the semiconductor layer 120 and a current flowing between the first electrode 131 and the second electrode 132 may vary.

As shown in FIG. 1, the semiconductor layer 120 may include a first semiconductor layer 121 disposed on the substrate 110 and including lightly-doped impurities, and second semiconductor layers 122 directly interposed between the first semiconductor layer 121 and the first and second electrodes 131 and 132 and including heavily-doped impurities. The second semiconductor layers 122 may have conductivity and may define a channel region within the first semiconductor layer 121. However, the inventive concept is not limited thereto, and the semiconductor layer 120 may be formed as a single layer formed of a semiconductor material and may include first and second impurity regions including heavily-doped impurities and a channel region including lightly-doped impurities between the first and second impurity regions.

The interlayer insulating layer 140 is disposed on the semiconductor layer 120 and the electrode layer 130 and has the first aperture 140op1 via which an upper surface of the first electrode 131 is exposed. The interlayer insulating layer 140 may be a single layer or multiple layers including an organic material having insulation properties. According to another example, the interlayer insulating layer 140 may be a single layer or multiple layers including an inorganic material. For example, the interlayer insulating layer 140 may include silicon oxide ($SiO_2$), silicon nitride (SiNx), silicon oxynitride (SiON), aluminum oxide ($Al_2O_3$), titanium oxide ($TiO_2$), tantalum oxide ($Ta_2O_5$), hafnium oxide ($HfO_2$), and/or zirconium oxide ($ZrO_2$). According to another example, the interlayer insulating layer 140 may include multiple layers including an inorganic insulating layer and an organic insulating layer.

The conductive layer 150 includes the upper surface light barrier unit 151 on the interlayer insulating layer 140 and the contact unit 152 buried within the first aperture 140op1. The upper surface light barrier unit 151 is disposed on the interlayer insulating layer 140 to cover the upper surface of the semiconductor layer 120. In a top view of the upper surface light barrier unit 151, the upper surface light barrier unit 151 may extend beyond the outer edge of the semiconductor layer 120 in order to completely cover the upper surface of the semiconductor layer 120. In a top view of the upper surface light barrier unit 151, the upper surface light barrier unit 151 may extend beyond the perimeter (e.g., the circumference) of the second electrode 132. As illustrated in FIG. 2A, the upper surface light barrier unit 151 may have a circular planar shape in correspondence with the shape of the outer edge of the semiconductor layer 120. However, the planar shape of the upper surface light barrier unit 151 is not limited to a circular shape, and may have various suitable planar shapes, such as a polygon and an oval.

The contact unit 152 extends from the upper surface light barrier unit 151 and is connected to the first electrode 131 via the first aperture 140op1. The contact unit 152 electrically connects the first electrode 131 to the upper surface light barrier unit 151.

The conductive layer 150 may be formed of a conductive material that does not transmit light. For example, the conductive layer 150 may be a single layer or multiple layers formed of a conductive material including molybdenum (Mo), aluminum (Al), copper (Cu), and/or titanium (Ti).

The upper surface light barrier unit 151 of the photosensitive thin film device 100 may block light that is radiated from above the upper surface light barrier unit 151 from reaching the upper surface of the semiconductor layer 120. Accordingly, light radiated from below the substrate 110 may reach the semiconductor layer 120, and electrical properties of the photosensitive thin film device 100 may vary depending on the amount of light radiated from below the substrate 110. For example, when a bias voltage is applied to the second electrode 132, the magnitude of current flowing from the second electrode 132 to the first electrode 131 may be proportional to the amount of light radiated from below the substrate 110 toward the semiconductor layer 120.

A portion of the light radiated from above the substrate 110 may reach the semiconductor layer 120. The light that is radiated from above the substrate 110 and that reaches the semiconductor layer 120 may correspond to noise of the photosensitive thin film device 100. However, according to the inventive concept, because most of the light radiated from above the substrate 110 is blocked, a noise component included in a current output from the photosensitive thin film device 100 may be reduced.

Further, the light radiated from below the substrate 110 may be light radiated from a light-emitting device located below the substrate 110, and/or may be light reflected by an object located below the substrate 110 from among light emitted from a light-emitting device located above the substrate 110.

Figure 2B:
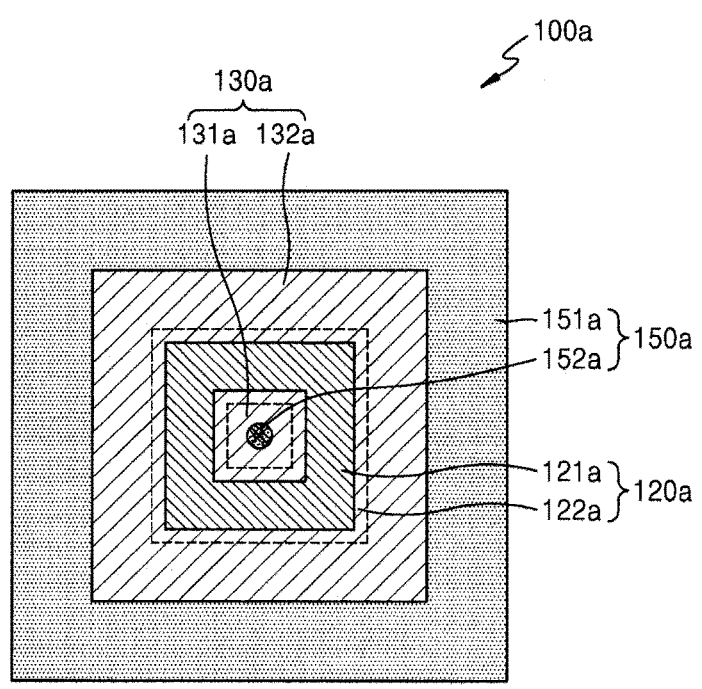
FIGS. 2B, 2C, and 2D are plan views of photosensitive thin film devices according to other embodiments of the present invention.
Figure 2C:
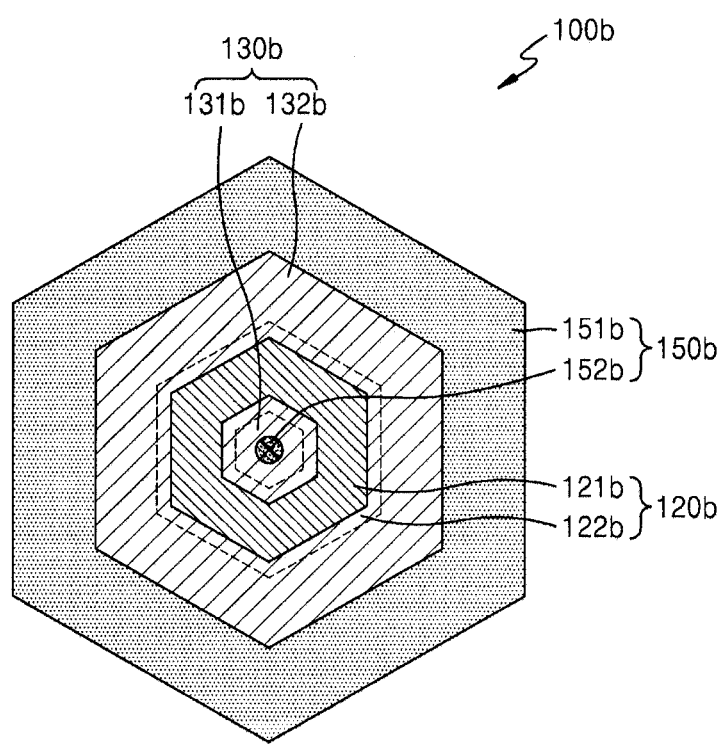
Figure 2D:
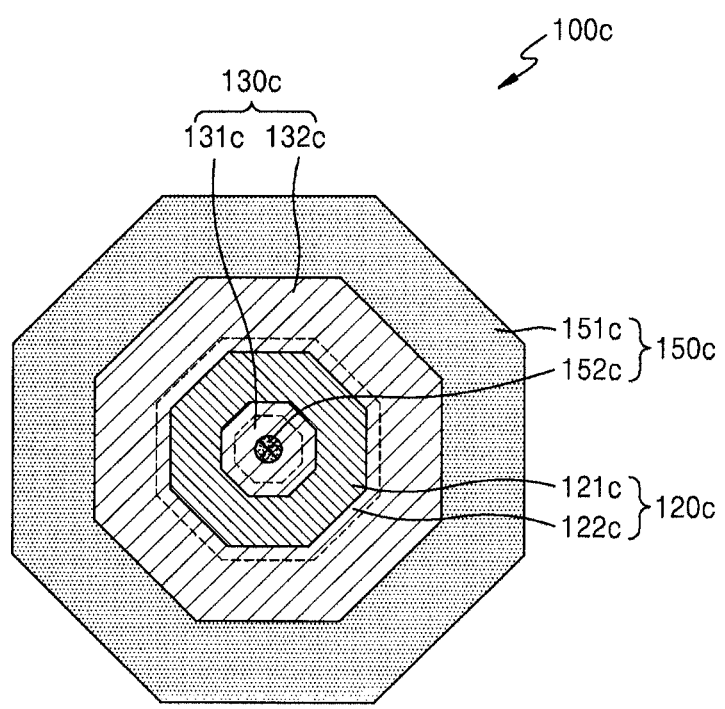

FIGS. 2B, 2C, and 2D are plan views of photosensitive thin film devices according to other embodiments of the present invention.

Referring to FIG. 2B, a photosensitive thin film device 100a includes a semiconductor layer 120a, an electrode layer 130a, and a conductive layer 150a. The semiconductor layer 120a, the electrode layer 130a, and the conductive layer 150a may correspond to the semiconductor layer 120, the electrode layer 130, and the conductive layer 150 of FIG.

2A, respectively, except for the planar shapes thereof. The description below will focus on the differences therebetween.

As shown in FIG. 2B, the semiconductor layer 120*a* may have a quadrilateral ring-type planar shape having a quadrilateral inner edge and a quadrilateral outer edge. For example, the inner edge and the outer edge of the semiconductor layer 120*a* may have various suitable planar shapes, such as a square, a rectangle, and a quadrilateral. The semiconductor layer 120*a* may include a first semiconductor layer 121*a* and second semiconductor layers 122*a*.

The electrode layer 130*a* includes a first electrode 131*a* and a second electrode 132*a*. The first electrode 131*a* is disposed inside the quadrilateral inner edge of the semiconductor layer 120*a*. The semiconductor layer 120*a* surrounds the perimeter of the first electrode 131*a*, and the first electrode 131*a* is electrically connected to the semiconductor layer 120*a*. As illustrated in FIG. 2B, the first electrode 131*a* may have a quadrilateral planar shape in correspondence with the shape of the quadrilateral inner edge of the semiconductor layer 120*a*.

The second electrode 132*a* is disposed to surround the perimeter of the semiconductor layer 120*a* and is electrically connected to the semiconductor layer 120*a*. As illustrated in FIG. 2B, the second electrode 132*a* may have a quadrilateral ring-type plane shape in correspondence with the shape of the quadrilateral outer edge of the semiconductor layer 120*a*.

The conductive layer 150*a* includes an upper surface light barrier unit 151*a* (e.g., an upper surface light barrier 151*a*) on the interlayer insulating layer 140, and a contact unit 152*a* (e.g., a contact plug 152*a*) buried within the first aperture 140*op*1. The upper surface light barrier unit 151*a* is disposed on the interlayer insulating layer 140 to cover the upper surface of the semiconductor layer 120*a*. In a top view, the upper surface light barrier unit 151*a* may extend beyond the quadrilateral outer edge of the semiconductor layer 120*a* in order to completely cover the upper surface of the semiconductor layer 120*a*. In a top view, the upper surface light barrier unit 151*a* may extend beyond the perimeter of the second electrode 132*a*. As illustrated in FIG. 2B, the upper surface light barrier unit 151*a* may have a quadrilateral planar shape in correspondence with the shape of the quadrilateral outer edge of the semiconductor layer 120*a*. However, the planar shape of the upper surface light barrier unit 151*a* is not limited to a quadrilateral, and may not correspond to the quadrilateral planar shape of the semiconductor layer 120*a*, namely, may correspond to a polygon other than a quadrilateral, an oval, or a circle.

Referring to FIG. 2C, a photosensitive thin film device 100*b* includes a semiconductor layer 120*b*, an electrode layer 130*b*, and a conductive layer 150*b*. The semiconductor layer 120*b*, the electrode layer 130*b*, and the conductive layer 150*b* may correspond to the semiconductor layer 120, the electrode layer 130, and the conductive layer 150 of FIG. 2A, respectively, except for planar shapes thereof. The description below will focus on the differences therebetween.

As shown in FIG. 2C, the semiconductor layer 120*b* may have a hexagonal ring-type planar shape having a hexagonal inner edge and a hexagonal outer edge. For example, the inner edge and the outer edge of the semiconductor layer 120*b* may have various suitable planar shapes, such as a regular hexagon or any irregular hexagon. The semiconductor layer 120*b* may include a first semiconductor layer 121*b* and second semiconductor layers 122*b*.

The electrode layer 130*b* includes a first electrode 131*b* and a second electrode 132*b*. The first electrode 131*b* is disposed inside the hexagonal inner edge of the semiconductor layer 120*b*. As illustrated in FIG. 2C, the first electrode 131*b* may have a hexagonal planar shape in correspondence with the shape of the hexagonal inner edge of the semiconductor layer 120*b*. The second electrode 132*b* is disposed to surround the perimeter of the semiconductor layer 120*b* and is electrically connected to the semiconductor layer 120*b*. As illustrated in FIG. 2C, the second electrode 132*b* may have a hexagonal ring-type planar shape in correspondence with the shape of the hexagonal outer edge of the semiconductor layer 120*b*.

The conductive layer 150*b* includes an upper surface light barrier unit 151*b* (e.g., an upper surface light barrier 151*b*) on the interlayer insulating layer 140, and a contact unit 152*b* (e.g., a contact plug 152*b*) buried within the first aperture 140*op*1. The upper surface light barrier unit 151*b* is disposed on the interlayer insulating layer 140 to cover the upper surface of the semiconductor layer 120*b*. As illustrated in FIG. 2C, the upper surface light barrier unit 151*b* may have a hexagonal planar shape in correspondence with the shape of the hexagonal outer edge of the semiconductor layer 120*b*. However, the planar shape of the upper surface light barrier unit 151*b* is not limited to a hexagon, and may not correspond to the hexagonal planar shape of the semiconductor layer 120*b*, namely, may correspond to a polygon other than a hexagon, an oval, or a circle.

Referring to FIG. 2D, a photosensitive thin film device 100*c* includes a semiconductor layer 120*c*, an electrode layer 130*c*, and a conductive layer 150*c*. The semiconductor layer 120*c*, the electrode layer 130*c*, and the conductive layer 150*c* may correspond to the semiconductor layer 120, the electrode layer 130, and the conductive layer 150 of FIG. 2A, respectively, except for planar shapes thereof. The description below will focus on the differences therebetween.

As shown in FIG. 2D, the semiconductor layer 120*c* may have an octagonal ring-type planar shape having an octagonal inner edge and an octagonal outer edge. For example, the inner edge and the outer edge of the semiconductor layer 120*c* may have various suitable planar shapes, such as a regular octagon or any irregular octagon. The semiconductor layer 120*c* may include a first semiconductor layer 121*c* and second semiconductor layers 122*c*.

The electrode layer 130*c* includes a first electrode 131*c* and a second electrode 132*c*. As illustrated in FIG. 2D, the first electrode 131*c* may be disposed inside the octagonal inner edge of the semiconductor layer 120*c* and thus have an octagonal planar shape. As illustrated in FIG. 2D, the second electrode 132*c* may have an octagonal ring-type planar shape in correspondence with the shape of the octagonal outer edge of the semiconductor layer 120*c*.

The conductive layer 150*c* includes an upper surface light barrier unit 151*c* (e.g., an upper surface light barrier 151*c*) on the interlayer insulating layer 140, and a contact unit 152*c* (e.g., a contact plug 152*c*) buried within the first aperture 140*op*1. As illustrated in FIG. 2D, the upper surface light barrier unit 151*c* may have an octagonal planar shape in correspondence with the shape of the octagonal outer edge of the semiconductor layer 120*c*. However, the planar shape of the upper surface light barrier unit 151*c* is not limited to an octagon, and may not correspond to the octagonal planar shape of the semiconductor layer 120*c*, namely, may correspond to a polygon other than an octagon, an oval, or a circle.

Figure 3:
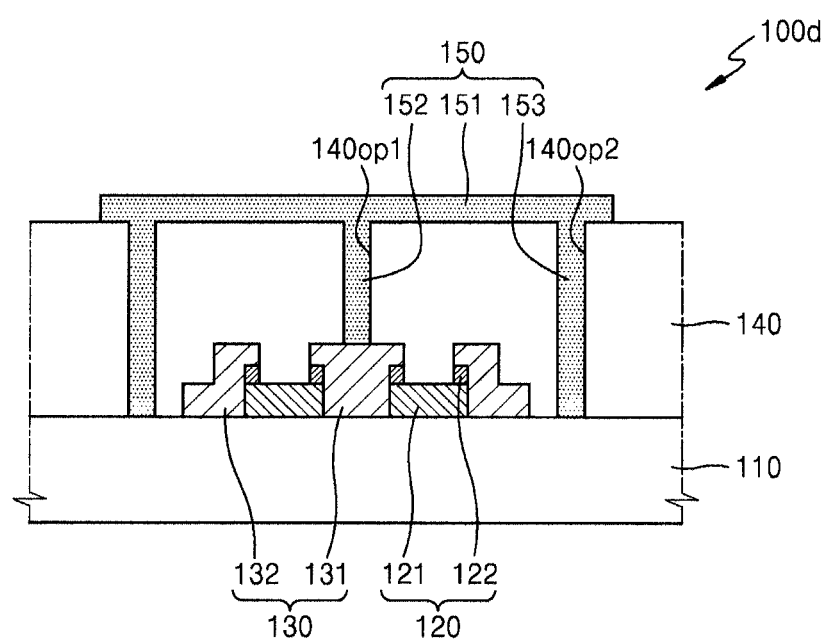
FIGS. 3 and 4 are respectively a cross-sectional view and a plan view of a photosensitive thin film device according to another embodiment of the present invention.
Figure 4:
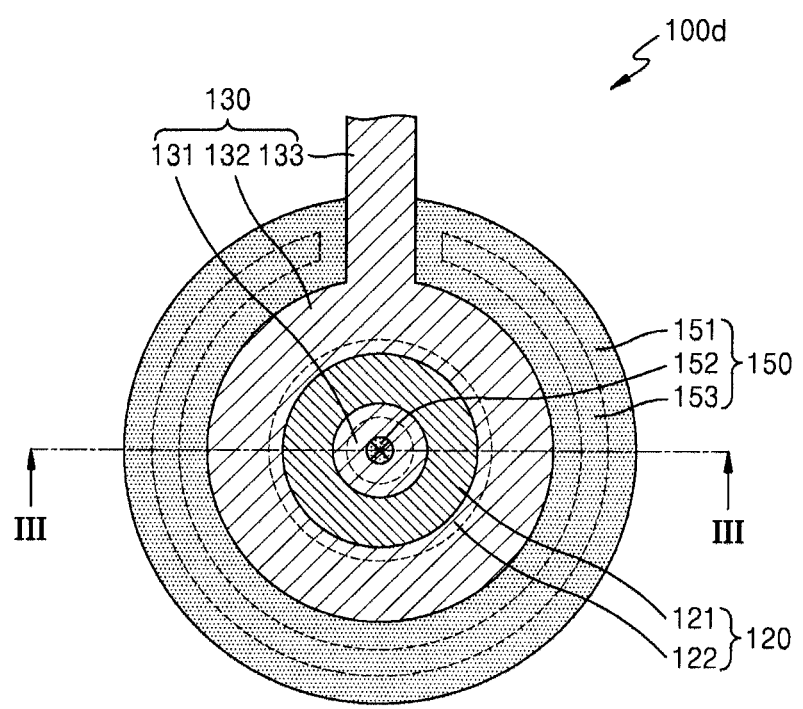

FIGS. 3 and 4 are respectively a cross-sectional view and a plan view of a photosensitive thin film device 100*d* according to another embodiment of the present invention. FIG. 3 is a cross-sectional view taken along the line of FIG. 4.

Referring to FIGS. 3 and 4, the photosensitive thin film device 100d is substantially the same as the photosensitive thin film device 100 of FIGS. 1 and 2A except that a lateral surface light barrier unit 153 (e.g., a lateral surface light barrier 153) and a connection line 133 are further included. Descriptions of the same or similar components may be omitted.

The electrode layer 130 may further include the connection line 133, which extends from the second electrode 132 in a lateral direction on the substrate 110. The connection line 133 may be integrally formed with the second electrode 132. The connection line 133 is provided to connect the second electrode 132 of the photosensitive thin film device 100d to another component on the substrate 110, for example, a thin film transistor.

The interlayer insulating layer 140 further includes a second aperture 140op2 spaced apart from the second electrode 132 in a lateral direction and surrounding a portion of the perimeter (e.g., the circumference) of the second electrode 132. As shown in FIG. 4, the second aperture 140op2 may have a planar shape such as an arc. A portion of the perimeter (e.g., the circumference) of the second electrode 132 that is not surrounded by the second aperture 140op2 is a portion that the connection line 133 contacts. When the second aperture 140op2 completely surrounds the perimeter (e.g., the circumference) of the second electrode 132, the connection line 133 on the same level as the second electrode 132 is exposed via the second aperture 140op2 and is electrically connected to the lateral surface light barrier unit 153. Accordingly, the second aperture 140op2 may surround the perimeter (e.g., the circumference) of the second electrode 132, as much as possible, without exposing the connection line 133.

The conductive layer 150 may further include the lateral surface light barrier unit 153, which fills the second aperture 140op2. The lateral surface light barrier unit 153 extends from the upper surface light barrier unit 151 along the second aperture 140op2. Accordingly, the lateral surface light barrier unit 153 is disposed to cover a portion of a lateral surface of the semiconductor layer 120 in a lateral direction. The lateral surface light barrier unit 153 may prevent light traveling in a lateral direction or light traveling in a diagonal direction from reaching the semiconductor layer 120. Thus, the upper surface light barrier unit 151 and the lateral surface light barrier unit 153 may block most of the light radiated from above the substrate 110.

The connection line 133 may extend in a lateral direction from the second electrode 132 via a hole in the plane of the lateral surface light barrier unit 153 having a planar shape, such as an arc, as shown in FIG. 4, and may be electrically insulated from the lateral surface light barrier unit 153 by the interlayer insulating layer 140.

Figure 5:
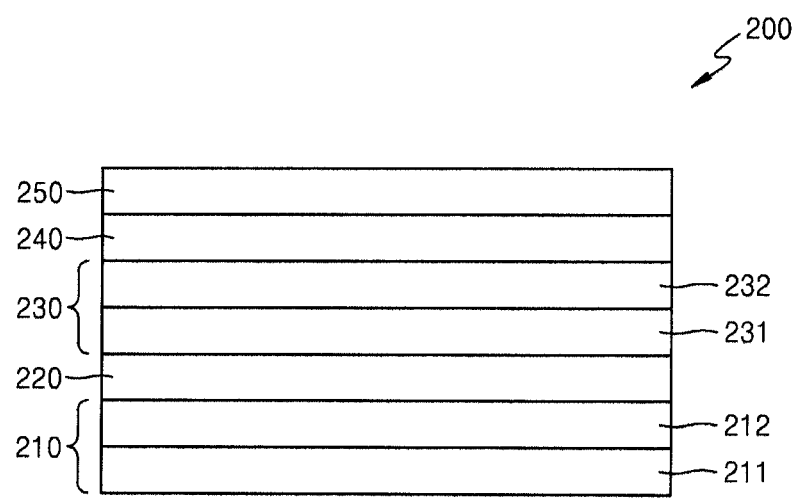
FIG. 5 is a schematic cross-sectional view of a biometric information sensing apparatus according to an embodiment of the present invention.

FIG. 5 is a schematic cross-sectional view of a biometric information sensing apparatus 200 according to an embodiment of the present invention.

Referring to FIG. 5, the biometric information sensing apparatus 200 includes a sensing unit 210 (e.g., a sensor 210) and a light source unit 230 (e.g., a light source 230). The sensing unit 210 includes a first substrate 211, and a light sensor array 212 on the first substrate 211. The light source unit 230 includes a second substrate 231 that is transparent and insulative and is disposed on the light sensor array 212, and a light-emission unit 232, for emitting light, on the second substrate 231.

The first and second substrates 211 and 231 may be formed of any of various suitable transparent and insulative materials, such as glass or plastic. According to an embodiment, each of the first substrate 211 and the second substrate 231 may include a flexible substrate that may be easily bent, folded, and/or rolled, and may be formed of ultrathin glass or plastic. For example, the first substrate 211 and the second substrate 231 may include, but are not limited to, at least one plastic material including PI, polyethyeleneterepthalate (PET), polyethyelenen napthalate (PEN), polycarbonate (PC), polyacrylate (PAR), polyetherimide (PEI), polyethersulphone (PES), polyphenylene sulfide (PPS), polyallylate, cellulose triacetate (TAC), cellulose acetate propionate (CAP), polydimethylsiloxane (PDMS), and/or hexamethyldisiloxane (HMDSO).

Accordingly, the biometric information sensing apparatus 200 may be bendable.

The light sensor array 212 is disposed on an upper surface of the first substrate 211. A body target, for which biometric information is to be sensed by the biometric information sensing apparatus 200, is arranged adjacent to a lower surface of the first substrate 211. For example, the body target may contact the lower surface of the first substrate 211. Light emitted from the light source unit 230 may be radiated toward the first substrate 211, reflected by the body target on the lower surface of the first substrate 211, and sensed by the light sensor array 212 of the sensing unit 210. The light radiated from the light source unit 230 toward the first substrate 211 passes through the sensing unit 210. The sensing unit 210 senses light reflected by the body target rather than light directly radiated thereonto by the light source unit 230, as much as possible.

The light sensor array 212 includes a plurality of unit pixels (e.g., a plurality of pixels) arranged in a matrix form on the first substrate 211, and each of the unit pixels includes a photosensitive thin film device. The photosensitive thin film device includes a first semiconductor pattern of a ring type having an inner edge and an outer edge on the first substrate 211, a first electrode disposed inside the inner edge of the first semiconductor pattern on the first substrate 211 and connected to the first semiconductor pattern, a second electrode surrounding the perimeter of the first semiconductor pattern along the outer edge of the first semiconductor pattern, an interlayer insulating layer disposed on the first semiconductor pattern and the first and second electrodes and having a first aperture via which the first electrode is exposed, and a light barrier electrode including an upper surface light barrier unit and a contact unit.

The upper surface light barrier unit is disposed on the interlayer insulating layer to cover an upper surface of the first semiconductor pattern and blocks light emitted from the light-emission unit from reaching the first semiconductor pattern. The contact unit extends from the upper surface light barrier unit and is connected to the first electrode along the first aperture. The photosensitive thin film device may be a photosensitive thin film device described above with reference to FIGS. 1 through 4. The light sensor array 212 will be described later in more detail with reference to FIGS. 6 through 9E.

The light-emission unit 232 is disposed on the second substrate 231 and emits light. The light-emission unit 232 may include a light-emission device that emits light that is radiated to the first substrate 211. The light-emission unit 232 may include a plurality of light-emitting devices, and the light-emitting devices may be arranged on the second substrate 231. The light-emission unit 232 may include a plurality of light-emitting devices that emit different types of lights. For example, the light-emission unit 232 may include a first light-emitting device that emits visible light of a first color, a second light-emitting device that emits visible light of a second color, and a third light-emitting device that emits infrared light. For example, the first color may be red, and the second color may be green. However, this is only an example, and the light-emission unit 232 may include light-emitting devices of one type and/or may emit lights of other colors or in other wavelength bands than the red and green visible lights and the infrared light.

For example, the light-emission unit 232 may include a light-emitting diode (LED), an organic light-emitting diode (OLED), or an electroluminescence device. The light-emitting devices may be regularly arranged in a matrix form on the second substrate 231. According to another example, the light-emitting devices may be arranged at regular intervals on an edge of the second substrate 231. In this case, the second substrate 231 may serve as a light guide plate that guides light emitted from the light-emitting devices of the light-emission unit 232 toward the first substrate 211. For example, the light-emission unit 232 may be a backlight unit (e.g., a backlight).

An adhesion layer 220 may be disposed between the sensing unit 210 and the light source unit 230. The adhesion layer 220 may be made transparent so that light emitted from the light source unit 230 illuminates the sensing unit 210. The adhesion layer 220 may bond the light source unit 230 onto the sensing unit 210.

A protection layer 250 may be disposed on the light source unit 230. The protection layer 250 protects the sensing unit 210 and the light source unit 230 therebelow, and may be formed of glass, plastic, metal, and/or the like. The protection layer 250 may include a reflection layer having light reflection characteristics so that light emitted from the light source unit 230 toward the protection layer 250 is reflected toward the first substrate 211. For example, the protection layer 250 may include a metal reflection layer formed of silver (Ag), magnesium (Mg), aluminum (Al), platinum (Pt), palladium (Pd), gold (Au), nickel (Ni), neodymium (Nd), iridium (Ir), and/or chromium (Cr).

The protection layer 250 may be bonded to the light source unit 230 by an adhesion layer 240. The adhesion layer 240 may have insulative characteristics. When the protection layer 250 has light reflection characteristics, the adhesion layer 240 may be transparent. The adhesion layer 240 may have light reflection characteristics. The protection layer 250 may be omitted according to the type of biometric information sensing apparatus 200. Further, according to the type of light source unit 230, the protection layer 250 may be directly formed on the light source unit 230 without having the adhesion layer 240 therebetween.

The biometric information sensing apparatus 200 may be any type of device including, for example, the light sensor array 212 and the light-emission unit 232 in the structure illustrated in FIG. 5. The biometric information sensing apparatus 200 may be an independent device for sensing biometric information. In this case, the biometric information sensing apparatus 200 may be flexible. For example, the biometric information sensing apparatus 200 may be wound around a body of a human, for example, a wrist, and may sense biometric information, such as a pulse wave, a heart rate, and/or oxygen saturation, from the wrist.

The biometric information sensing apparatus 200 may be a component that is provided on a portable terminal, such as a smartphone or a notebook, having a function of sensing biometric information. The biometric information sensing apparatus 200 for sensing biometric information may be arranged on a rear surface of a portable terminal, for example, a smartphone. In this case, when a user holds the smartphone with his or her hand, the palm of the user may contact the lower surface of the first substrate 211 of the biometric information sensing apparatus 200, and the biometric information sensing apparatus 200 may sense biometric information, such as a vein pattern, from the palm of the user. A controller of the smartphone may use the sensed biometric information in user authentication.

Figure 6:
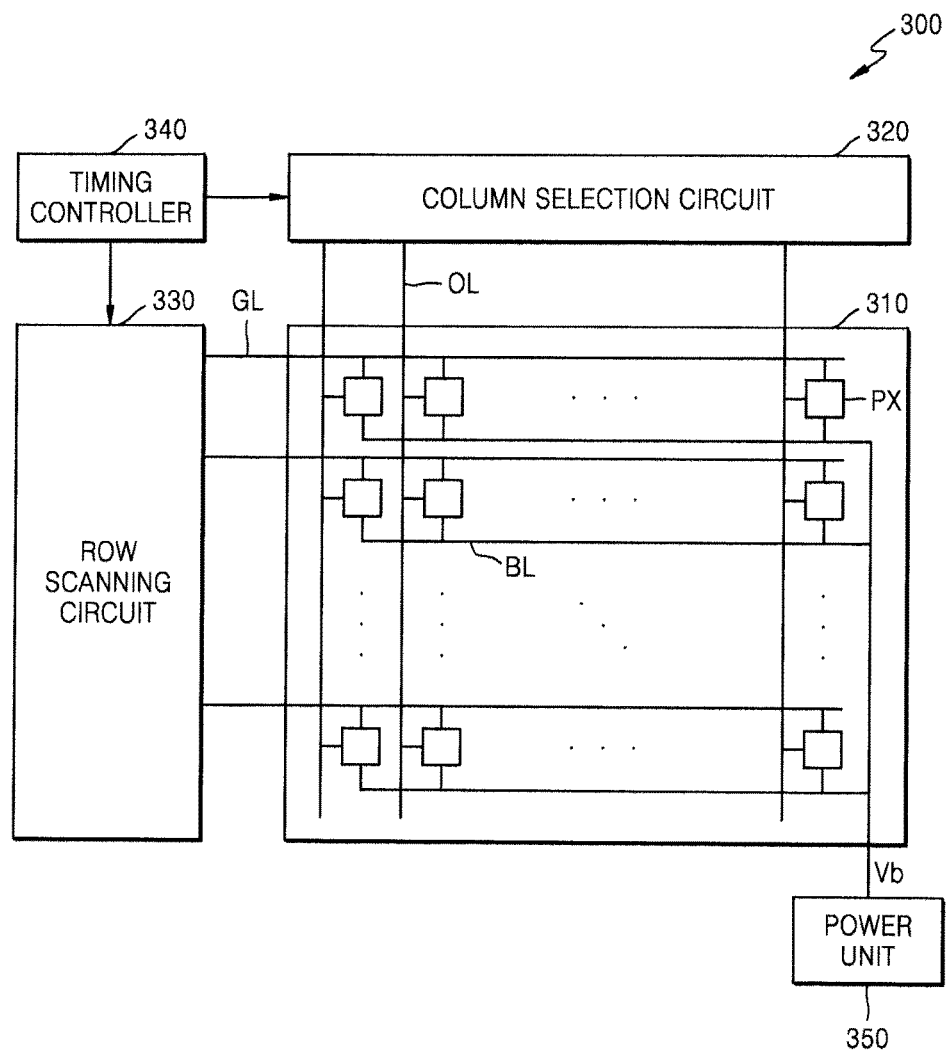
FIG. 6 is a schematic block diagram of an image sensor including a light sensor array, according to an embodiment of the present invention.

FIG. 6 is a schematic block diagram of an image sensor 300 including a light sensor array 310, according to an embodiment of the present invention.

Referring to FIG. 6, the image sensor 300 includes the light sensor array 310, a column selection circuit 320, a row scanning circuit 330, a timing controller 340, and a power unit 350 (e.g., a power supply 350). The light sensor array 310 may correspond to the light sensor array 212 of FIG. 5. The column selection circuit 320 and the row scanning circuit 330 may be disposed within the light sensor array 212 of FIG. 5, and the timing controller 340 and the power unit 350 may be disposed outside the stacked structure of FIG. 5. However, the inventive concept is not limited thereto, and the column selection circuit 320 and the row scanning circuit 330 may be disposed outside the stacked structure of FIG. 5. The column selection circuit 320, the row scanning circuit 330, and the timing controller 340 may be collectively referred to as an image sensor controller.

The light sensor array 310 may include a plurality of unit pixels PX (e.g., a plurality of pixels) arranged in a matrix form. The light sensor array 310 may include gate lines GL each connected to unit pixels PX on an identical row (e.g., a same row) from among the plurality of unit pixels PX, output lines OL each connected to unit pixels PX on an identical column (e.g., a same column) from among the plurality of unit pixels PX, and a bias line BL connected to the plurality of unit pixels PX. As shown in FIG. 6, the gate lines GL may extend in a row direction, and the output lines OL may extend in a column direction. The bias line BL may extend in a row direction as shown in FIG. 6, but this is an example. The bias line BL may extend in a column direction, similar to the output lines OL. The row direction denotes a horizontal direction and the column direction denotes a vertical direction, but the inventive concept is not limited thereto.

A unit pixel PX (e.g., a pixel PX) outputs to an output line OL a signal having a magnitude proportional to light incident thereon. The signal output by the unit pixel PX to the output line OL may be a current signal or a voltage signal. The unit pixel PX may include one of the photosensitive thin film devices 100 through 100d and a thin film transistor TFT of FIG. 7. The number of thin film transistors TFT may vary depending on a pixel circuit of the unit pixel PX. The unit pixel PX according to an embodiment will be described later in more detail with reference to FIGS. 7 through 9E.

The timing controller 340 may control the column selection circuit 320 and the row scanning circuit 330, and may supply control signals, such as a clock signal and a timing control signal, used during operations of the column selection circuit 320 and the row scanning circuit 330. The timing controller 340 may include, for example, a logic control circuit, a phase locked loop (PLL) circuit, a timing control circuit, and a communication interface circuit.

The row scanning circuit 330 may receive control signals from the timing controller 340 and control a row address and a row scan of the light sensor array 310. In order to select a gate line GL from the plurality of gate lines GL, the row scanning circuit 330 may output a signal for selecting the gate line GL to the light sensor array 310. The row scanning circuit 330 may sequentially drive the gate lines GL. The row scanning circuit 330 may include, for example, a row decoder that selects the gate lines GL within the light sensor array 310, and a row driver that provides a signal for activating the selected gate lines GL.

The column selection circuit 320 may receive control signals from the timing controller 340, receive a sensing signal output via the output lines OL from unit pixels PX connected to an activated gate line GL within the light sensor array 310, convert the received sensing signal into a digital signal, and output the digital signal to the timing controller 340. The column selection circuit 320 may include analog-to-digital converters (ADCs) in order to convert sensing signals output via the output lines OL into digital signals. The column selection circuit 320 may further include a column decoder for selecting the ADCs, and a column driver for transmitting a digital signal output from an ADC to a horizontal transmission line.

The timing controller 340 may generate image data, based on a digital signal received from the column selection circuit 320 and an address of a unit pixel PX (e.g., a pixel PX) determined by selected gate lines GL and an output line via which a sensing signal was received. In other words, the image sensor controller including the column selection circuit 320, the row scanning circuit 330, and the timing controller 340 may sequentially drive the gate lines GL, receive sensing signals output by the unit pixels PX via the output lines OL, and generate image data based on the sensing signals.

The power unit 350 provides the bias line BL with a bias voltage Vb. The bias voltage Vb is applied to the unit pixels PX in order to drive the unit pixels PX. The unit pixels PX may output a current signal or voltage signal having a magnitude proportional to the intensity of radiated light, to output lines OL corresponding to the unit pixels PX.

Figure 7:
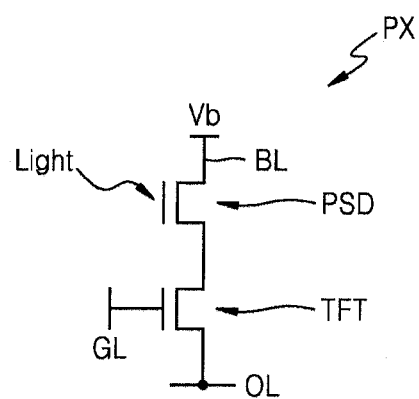
FIG. 7 is a circuit diagram of a unit pixel within a light sensor array, according to an embodiment of the present invention.

FIG. 7 is a circuit diagram of a unit pixel PX (e.g., a pixel PX) within the light sensor array 310, according to an embodiment of the present invention.

Referring to FIG. 7, the unit pixel PX includes a photosensitive thin film device PSD and the thin film transistor TFT. The photosensitive thin film device PSD may correspond to one of the photosensitive thin film devices 100 through 100d described above with reference to FIGS. 1 through 4.

The bias voltage Vb is applied to a first electrode of the photosensitive thin film device PSD. A second electrode of the photosensitive thin film device PSD is connected to the thin film transistor TFT. Resistance of the photosensitive thin film device PSD varies depending on the amount of light radiated to a semiconductor layer of the photosensitive thin film device PSD. When the amount of light radiated to the semiconductor layer increases, carriers increase within the semiconductor layer and resistance between the first electrode and the second electrode of the photosensitive thin film device PSD decreases. Consequently, a current flowing between the first electrode and the second electrodes increases.

A first electrode of the thin film transistor TFT is connected to the second electrode of the photosensitive thin film device PSD. A second electrode of the thin film transistor TFT is connected to an output line OL. A gate line GL is connected to a gate of the thin film transistor TFT, and the thin film transistor TFT is turned on in response to a gate signal received via the gate line GL. When the thin film transistor TFT is turned on, a current received from the photosensitive thin film device PSD is transmitted to the output line OL via the turned-on thin film transistor TFT.

The column selection circuit 320 of FIG. 6 may sense the current received from the output line OL, convert the magnitude of the sensed current into a digital signal, and provide the digital signal to the timing controller 340. The timing controller 340 may generate image data, based on an address of the unit pixel PX and the digital signal.

Figure 8:
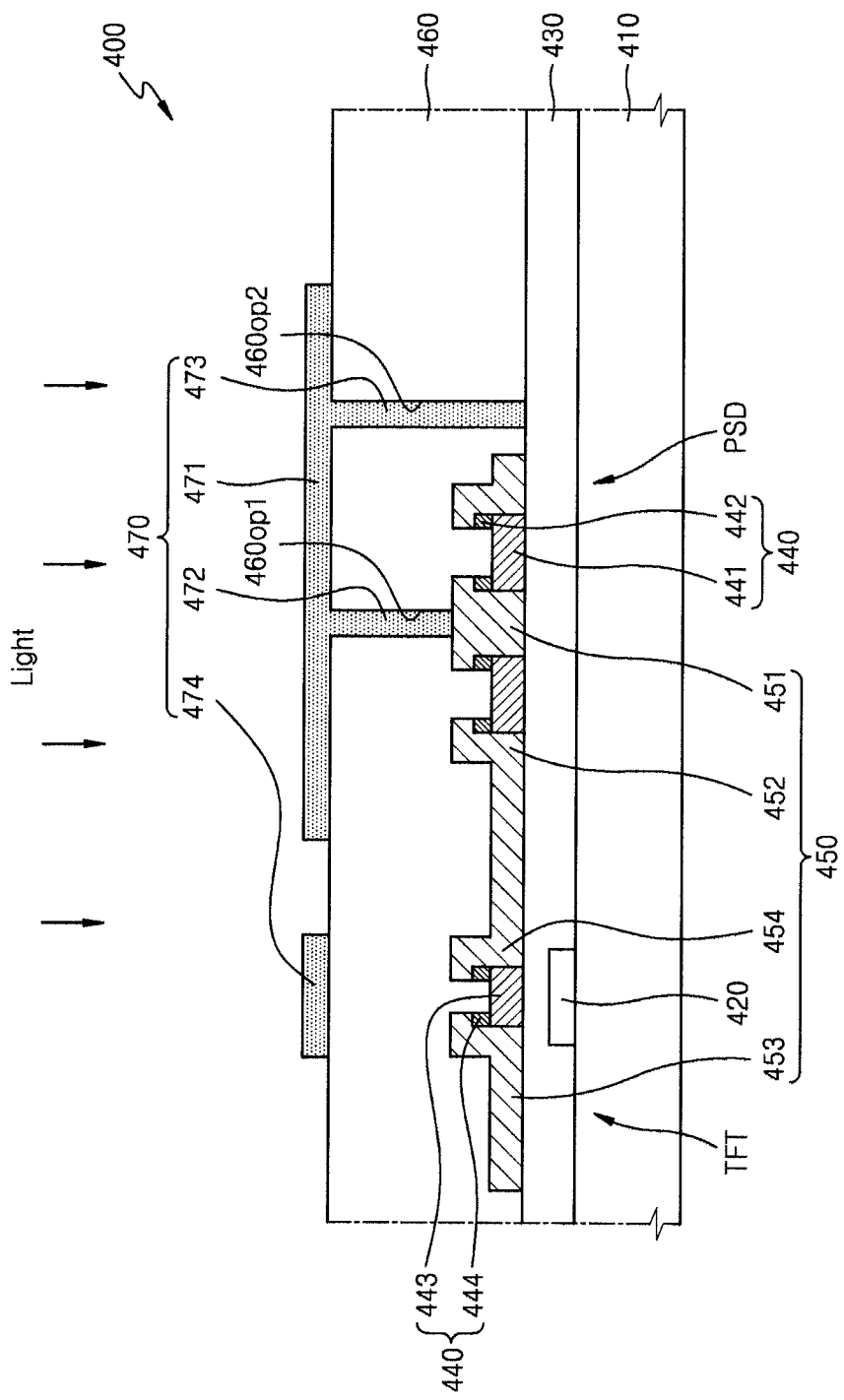
FIG. 8 is a cross-sectional view of a unit pixel according to an embodiment of the present invention.
Figure 9A:
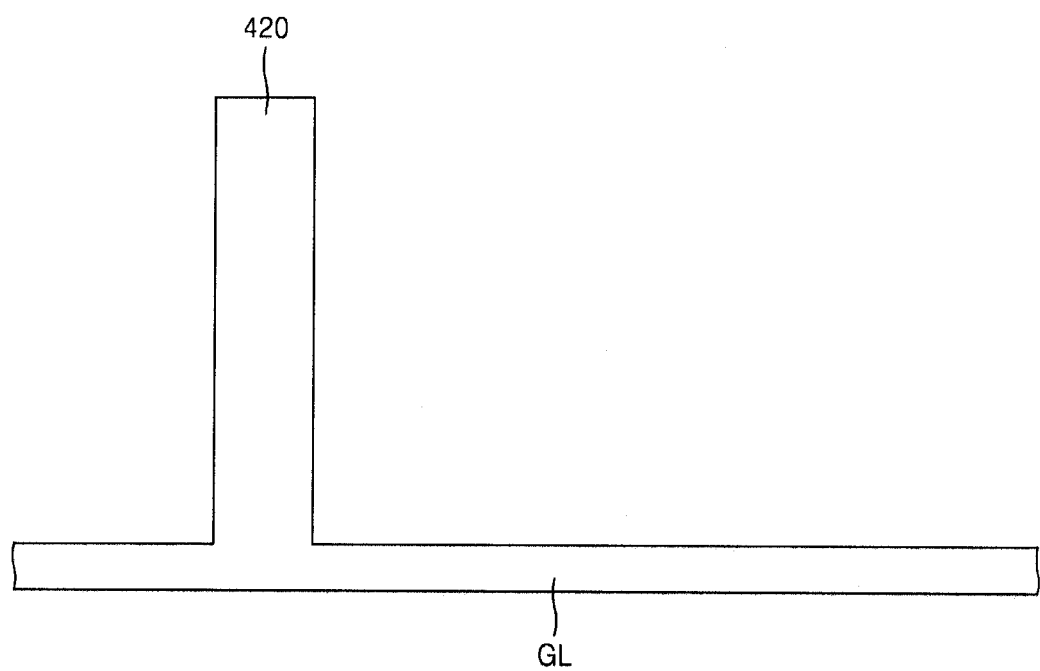
FIGS. 9A, 9B, 9C, 9D, and 9E are plan views of a method of manufacturing the unit pixel according to the embodiment of FIG. 8.
Figure 9B:
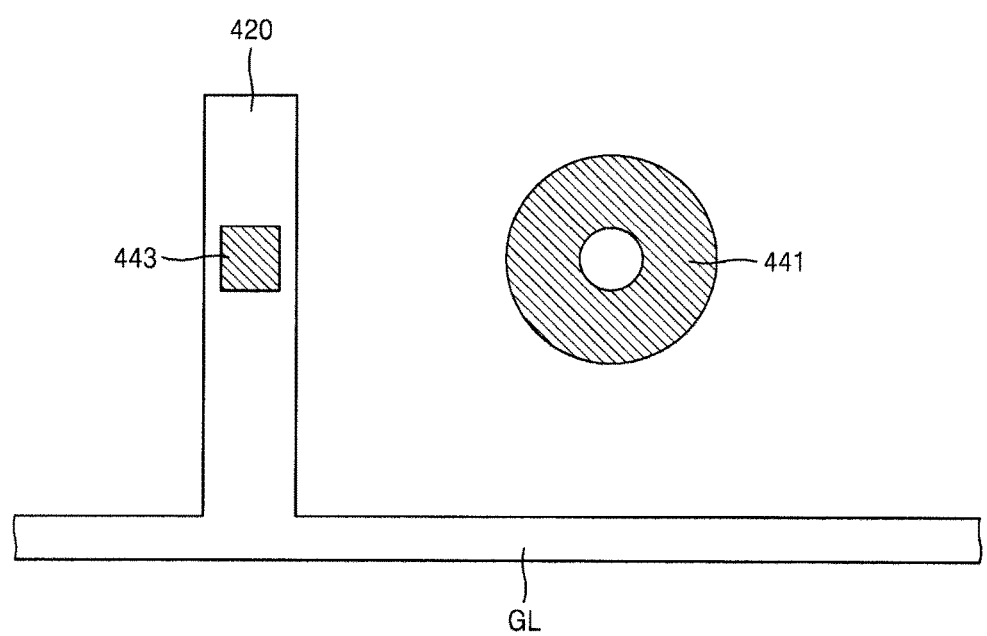
Figure 9C:
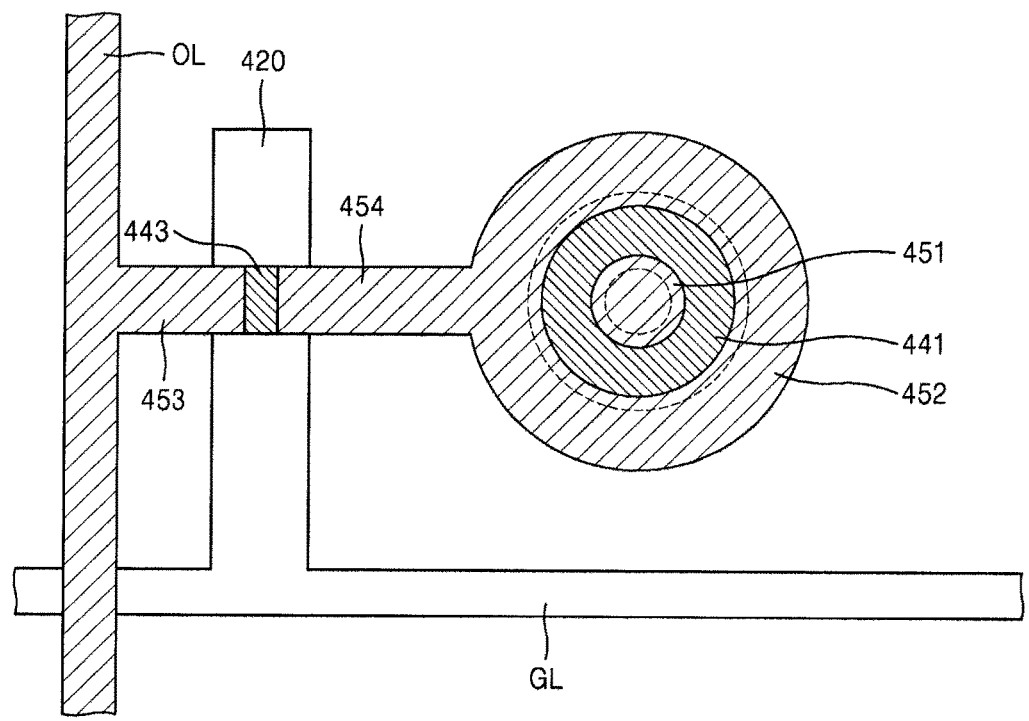

FIG. 8 is a cross-sectional view of a unit pixel according to an embodiment of the present invention and FIGS. 9A through 9E are plan views of a unit pixel 400 (e.g., a pixel 400) according to the embodiment of FIG. 8. FIG. 8 is a cross-sectional view taken along the line VIII-VIII of FIG. 9E. FIG. 9A is a plan view of a first conductive layer including a gate electrode of the unit pixel 400. FIG. 9B is a plan view of a semiconductor layer on the first conductive layer. FIG. 9C is a plan view of a second conductive layer including first through fourth electrodes on the semiconductor layer.

Figure 9D:
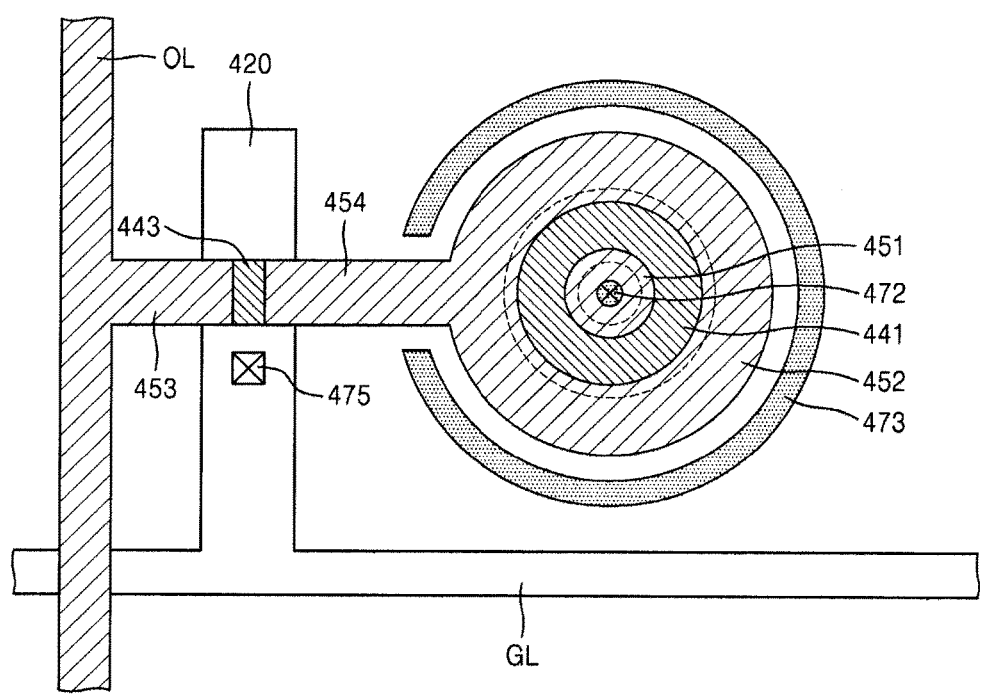
Figure 9E:
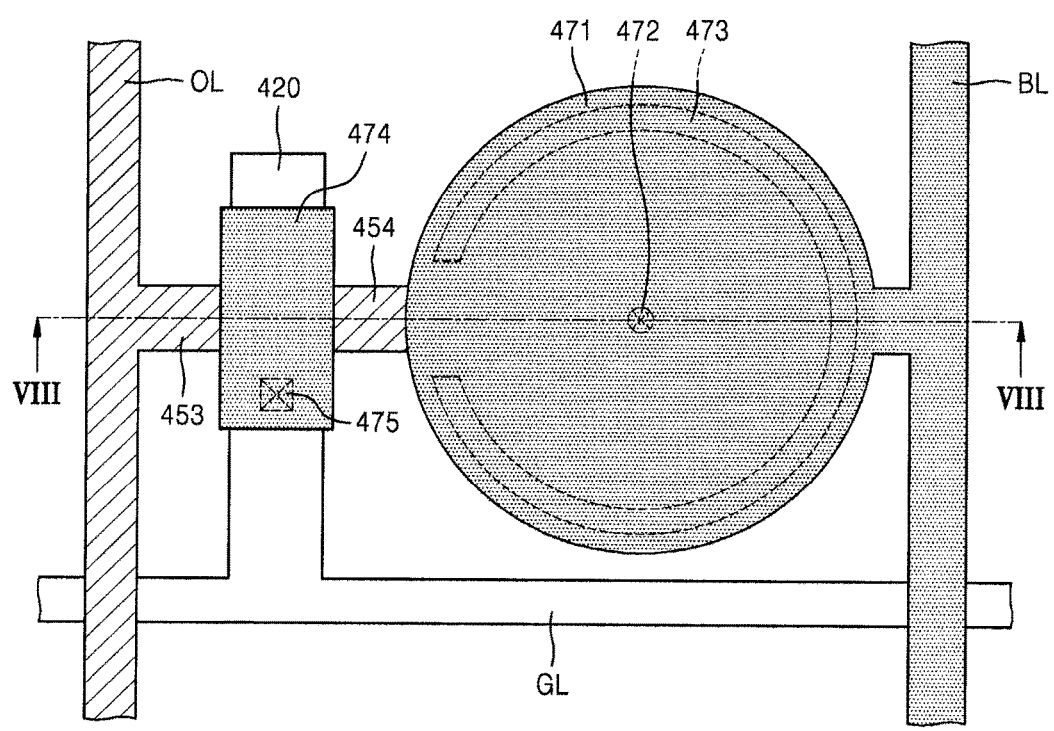

FIG. 9D is a plan view of a contact unit and a lateral surface light barrier unit, which are portions of a third conductive layer on the second conductive layer. FIG. 9E is a plan view of the third conductive layer including an upper surface light barrier unit on the second conductive layer.

Referring to FIGS. 8 and 9A through 9E together with FIGS. 5 through 7, the unit pixel 400 includes a photosensitive thin film device PSD and a thin film transistor TFT disposed on a substrate 410. The unit pixel 400 is an example, and embodiments of the present invention may have another circuit structure including two or more thin film transistors TFT.

The unit pixel 400 includes a substrate 410, a first conductive layer including a first gate electrode 420 of the thin film transistor TFT, a semiconductor layer 440 including first and second semiconductor patterns 441 and 443, a second conductive layer 450 including first through fourth electrodes 451 through 454, and a third conductive layer 470 including an upper surface light barrier unit 471 (e.g., an upper surface light barrier 471), a contact unit 472 (e.g., a contact plug 472), a lateral surface light barrier unit 473 (e.g., a lateral surface light barrier 473), and a second gate electrode 474. The unit pixel 400 further includes a gate insulating layer 430 between the first gate electrode 420 and the second semiconductor pattern 443, and an interlayer insulating layer 460 between the semiconductor layer 440 and the second conductive layer 450. Light is radiated from above, namely, from the light-emission unit 232 of FIG. 5, to the unit pixel 400, and the light is reflected by a body below the substrate 410 and reaches the first semiconductor pattern 441.

Although the photosensitive thin film device PSD illustrated in FIGS. 8 and 9A through 9E has the same or substantially the same structure as the photosensitive thin film device 100d of FIGS. 3 and 4, this is only an example, and embodiments of the present invention are not limited thereto. For example, the photosensitive thin film device PSD illustrated in FIGS. 8 and 9A through 9E may be replaced by the photosensitive thin film device 100 of FIGS. 1 and 2A.

The substrate 410 may include a base substrate formed of any of various suitable transparent and insulative materials, such as glass or plastic, According to an embodiment, the substrate 410 may include a flexible base substrate that may be easily bent, folded, and/or rolled. For example, the substrate 410 may include a flexible base substrate formed of ultra-thin glass or plastic. For example, the substrate 410 may include a base substrate formed of, but is not limited to, at least one plastic material including polyimide (PI), polyethyeleneterepthalate (PET), polyethyelenen napthalate (PEN), polycarbonate (PC), polyacrylate (PAR), polyetherimide (PEI), polyethersulphone (PES), polyphenylene sulfide (PPS), polyallylate, cellulose triacetate (TAC), cellulose acetate propionate (CAP), polydimethylsiloxane (PDMS), and/or hexamethyldisiloxane (HMDSO).

The substrate 410 may further include a buffer layer on the base substrate. The buffer layer may prevent permeation of impure elements and may planarize the surface of the base substrate. A barrier layer may be interposed between the base substrate and the buffer layer of the substrate 410. When a buffer layer and/or a barrier layer formed of an insulative material are disposed on the base substrate, the base substrate may be formed of conductive transparent metal or metal oxide.

Unit pixels PX, each including a photosensitive thin film device PSD and a thin film transistor TFT, may be arranged in a matrix form on the substrate 410.

Light radiated from above the unit pixel 400 may be reflected by a lower surface of the substrate 410 and may reach the first semiconductor pattern 441. Because only light reflected by a body below the substrate 410 should reach the first semiconductor pattern 441, light reflected by the lower surface of the substrate 410 and incident upon the first semiconductor pattern 441 and light incident upon the first semiconductor pattern 441 while traveling along the substrate 410 in a lateral direction should be reduced or minimized.

The light reflected by the lower surface of the substrate 410 and incident upon the first semiconductor pattern 441 and the light incident upon the first semiconductor pattern 441 while traveling along the substrate 410 in a lateral direction may be about 50% of light sensed by the photosensitive thin film device PSD. These lights may act as noise. The substrate 410 may have a thickness for reducing or minimizing such noise. For example, the substrate 410 may have a thickness of 50 μm or less. For example, the substrate 410 may have a thickness of 25 μm or less. According to an experiment, the noise when the substrate 410 has a thickness of 50 μm was about 40% of the noise when the substrate 410 has a thickness of 500 μm. The noise when the substrate 410 has a thickness of 25 μm was about 70% of the noise when the substrate 410 has a thickness of 500 μm.

The first conductive layer including the first gate electrode 420 of the thin film transistor TFT is disposed on the substrate 410. The first conductive layer may include a gate line GL extending in a row direction. The first gate electrode 420 may be a portion of the gate line GL and thus may be formed together with the gate line GL. The gate line GL may extend in a row direction and may be connected to the row scanning circuit 330. The first conductive layer may be a single layer or multiple layers formed of a conductive material including molybdenum (Mo), aluminum (Al), copper (Cu), and/or titanium (Ti).

The gate insulating layer 430 is disposed on the first conductive layer. The gate insulating layer 430 may be a single layer or multiple layers including an inorganic material having insulation properties. For example, the gate insulating layer 430 may include silicon oxide ($SiO_2$), silicon nitride (SiNx), silicon oxynitride (SiON), aluminum oxide ($Al_2O_3$), titanium oxide ($TiO_2$), tantalum oxide ($Ta_2O_5$), hafnium oxide ($HfO_2$), and/or zinc oxide ($ZnO_2$). As another example, the gate insulating layer 430 may be a single layer or multiple layers including an organic material having insulation properties. As another example, the gate insulating layer 430 may have a multi-layered structure in which an organic insulation material alternates with an inorganic insulation material.

The semiconductor layer 440, including the first semiconductor pattern 441 functioning as a photosensitive layer of the photosensitive thin film device PSD and the second semiconductor pattern 443 functioning as an active layer of the thin film transistor TFT, is arranged on the gate insulating layer 430.

The first semiconductor pattern 441 may have a ring-type planar shape having an inner edge and an outer edge. As shown in FIG. 9B, the first semiconductor pattern 441 may have a circular ring-type planar shape having a circular inner edge and a circular outer edge. However, the inner edge and the outer edge of the first semiconductor pattern 441 are not limited to a circular shape, and may have various suitable planar shapes, such as a polygon and an oval. For example, the first semiconductor pattern 441 may have a rectangular frame-type planar shape.

When the first semiconductor pattern 441 has a circular ring-type planar shape, a radius of an outer edge thereof may be 60 to 120 μm. In detail, the radius of the outer edge may be 80 to 100 μm. When the first semiconductor pattern 441 has an overly wide area, the amount of light that is emitted from the light-emission unit 232 of FIG. 5 and that reaches the body below the substrate 410 decreases. On the other hand, when the first semiconductor pattern 441 has an overly narrow area, the amount of light that is emitted from the light-emission unit 232 of FIG. 5 and reaches the body below the substrate 410 increases, but the amount of light that is reflected by the body and reaches the first semiconductor pattern 441 decreases. According to an experiment, when the radius of the outer edge was 80 to 100 μm, the amount of light sensed by the photosensitive thin film device PSD was high (e.g., maximum). In this experiment, a resolution (or a density) of the unit pixel was 100 dpi.

When the first semiconductor pattern 441 is irradiated with light, electrons within the first semiconductor pattern 441 are excited from a valence band to a conduction band. Accordingly, the first semiconductor pattern 441 becomes conductive, and the first electrode 451 and the second electrode 452 are electrically connected to each other. Depending on the amount of light radiated onto the first semiconductor pattern 441, resistance of the first semiconductor pattern 441 may vary, and accordingly a current flowing between the first electrode 451 and the second electrode 452 may vary.

The second semiconductor pattern 443 is disposed on the substrate 410 such that it overlaps with at least a portion of the first gate electrode 420. The second semiconductor pattern 443 has a channel region. The channel region overlaps with the first gate electrode 420.

The semiconductor layer 440 may include a semiconductor material sensitive to visible light and/or infrared light, for example, amorphous silicon (a-Si) or amorphous silicon germanium (a-SiGe). According to another embodiment, the semiconductor layer 440 may include germanium (Ge), indium phosphide (InP), cadmium telluride (CdTe), or gallium arsenide (GaAs). According to another embodiment, the semiconductor layer 440 may include an organic semiconductor material and/or an oxide semiconductor material.

The semiconductor layer 440 may further include first conductive semiconductor patterns 442 and second conductive semiconductor patterns 444 having conductivity by including heavily doped impurities. The first conductive semiconductor patterns 442 are interposed directly between the first semiconductor pattern 441 and the first and second electrodes 451 and 452, and the second conductive semiconductor patterns 444 are interposed directly between the second semiconductor pattern 443 and the third and fourth electrodes 453 and 454. Thus, the second conductive semiconductor patterns 444 may define a channel region within the second semiconductor pattern 443. In this case, the second conductive semiconductor patterns 444 may include first and second impurity regions respectively positioned on both sides of the channel region. The semiconductor layer 440 may be formed as multiple layers including a first semiconductor layer comprised of the first and second semiconductor patterns 441 and 443 and a second semiconductor layer comprised of the first and second conductive semiconductor patterns 442 and 444. The inventive concept is not limited thereto, and the semiconductor layer 440 may be formed as a single layer formed of a semiconductor material and may include first and second impurity regions including heavily-doped impurities and a channel region including lightly-doped impurities between the first and second impurity regions.

The first electrode 451 is disposed inside an inner edge of the first semiconductor pattern 441 on the substrate 410, and is connected to the first semiconductor pattern 441 via the first conductive semiconductor patterns 442. The first semiconductor pattern 441 surrounds the perimeter (e.g., the circumference) of the first electrode 451, and the first electrode 451 is electrically connected to the first semiconductor pattern 441 via the first conductive semiconductor patterns 442. As illustrated in FIG. 8, the first electrode 451 may be disposed on the first semiconductor pattern 441 and the first conductive semiconductor patterns 442 such that it covers the inner edge of the first semiconductor pattern 441. However, the inventive concept is not limited thereto, and the first electrode 451 may be disposed below the first semiconductor pattern 441. As shown in FIG. 9C, the first electrode 451 may have a circular planar shape in correspondence with the shape of the inner edge of the first semiconductor pattern 441.

The second electrode 452 surrounds the perimeter (e.g., the circumference) of the first semiconductor pattern 441 along the outer edge of the first semiconductor pattern 441 on the substrate 410, and is electrically connected to the first semiconductor pattern 441 via the first conductive semiconductor patterns 442. As illustrated in FIG. 8, the second electrode 452 may be disposed on the first semiconductor pattern 441 and the first conductive semiconductor patterns 442 such that it covers the outer edge of the semiconductor layer 440. However, the inventive concept is not limited thereto, and the second electrode 452 may be disposed below the first semiconductor pattern 441. As shown in FIG. 9C, the second electrode 452 may have a ring-type planar shape in correspondence with the shape of the outer edge of the first semiconductor pattern 441.

The second electrode 452 may have a portion linearly extending on the substrate 410 so as to be connected to the fourth electrode 454 of the thin film transistor TFT. The linear extension of the second electrode 452 may be referred to as a connection electrode or a connection line.

The third electrode 453 may connect a first impurity region of the second semiconductor pattern 443 of the thin film transistor TFT, namely, a region corresponding to one side of the second conductive semiconductor patterns 444, to an output line OL. The output line OL may extend in a column direction as shown in FIG. 9C and may be connected to the column selection circuit 320.

The fourth electrode 454 may connect a second impurity region of the second semiconductor pattern 443 of the thin film transistor TFT, namely, a region corresponding to the other side of the second conductive semiconductor patterns 444, to the second electrode 452 of the photosensitive thin film device PSD.

The first through fourth electrodes 451 through 454 may be portions of the second conductive layer 450. The second conductive layer 450 may be referred to as an electrode layer. The second conductive layer 450 may be a single layer or multiple layers formed of a conductive material including molybdenum (Mo), aluminum (Al), copper (Cu), and/or titanium (Ti).

The interlayer insulating layer 460 is disposed on the semiconductor layer 440 and the second conductive layer 450 and has a first aperture 460op1 via which an upper surface of the first electrode 451 is exposed. As shown in FIGS. 8 and 9D, the interlayer insulating layer 460 may further include a second aperture 460op2 that surrounds a portion of the perimeter (e.g., the circumference) of the second electrode 452. Because the lateral surface light barrier unit 473 of FIG. 9D is defined as a portion that fills the second aperture 460op2, the second aperture 460op2 has substantially the same shape as the lateral surface light barrier unit 473 of FIG. 9D.

The second aperture 460op2 may be disposed to surround a portion other than the linear extension of the second electrode 452, which is connected to the fourth electrode 454.

The interlayer insulating layer 460 may further include an aperture for connecting the first gate electrode 420 to a portion of the third conductive layer 470, namely, to the second gate electrode 474, as indicated as a gate connection unit 475 (e.g., a gate connector 475) of FIG. 9D.

The interlayer insulating layer 460 may be a single layer or multiple layers including an organic material having insulation properties. According to another example, the interlayer insulating layer 460 may be a single layer or multiple layers including an inorganic material. For example, the interlayer insulating layer 460 may include silicon oxide ($SiO_2$), silicon nitride (SiNx), silicon oxynitride (SiON), aluminum oxide ($Al_2O_3$), titanium oxide ($TiO_2$), tantalum oxide ($Ta_2O_5$), hafnium oxide ($HfO_2$), and/or zirconium oxide ($ZrO_2$). According to another example, the interlayer insulating layer 460 may include multiple layers including an inorganic insulating layer and/or an organic insulating layer.

The third conductive layer 470 includes an upper surface light barrier unit 471 (e.g., an upper surface light barrier 471) and the second gate electrode 474 disposed on the interlayer insulating layer 460, and a contact unit 472 (e.g., a contact plug 472) and the lateral surface light barrier unit 473 respectively buried in the first aperture 460op1 and the second aperture 460op2.

The upper surface light barrier unit 471 is disposed on the interlayer insulating layer 460 to cover the upper surface of the first semiconductor pattern 441. In a top view of the upper surface light barrier unit 471, the upper surface light barrier unit 471 may extend beyond the outer edge of the first semiconductor pattern 441 in order to completely cover the upper surface of the first semiconductor pattern 441. In a top view of the upper surface light barrier unit 471, the upper surface light barrier unit 471 may extend beyond the perimeter (e.g., the circumference) of the second electrode 452. As illustrated in FIG. 9E, the upper surface light barrier unit 471 may have a circular planar shape in correspondence with the shape of the outer edge of the first semiconductor pattern 441.

The contact unit 472 extends from the upper surface light barrier unit 471 and is connected to the first electrode 451 via the first aperture 460op1. The contact unit 472 electrically connects the first electrode 451 to the upper surface light barrier unit 471.

The lateral surface light barrier unit 473 is buried in the second aperture 460op2 of the third conductive layer 470. The lateral surface light barrier unit 473 extends from the upper surface light barrier unit 471 along the second aperture 460op2. The lateral surface light barrier unit 473 is disposed to cover a portion of a lateral surface of the first semiconductor pattern 441 in a lateral direction. The lateral surface light barrier unit 473 may prevent light traveling in a lateral direction or light traveling in a diagonal direction from reaching the first semiconductor pattern 441.

At least a portion of the second gate electrode 474 is disposed on the interlayer insulating layer 460 to overlap with the channel region of the second semiconductor pattern 443. As illustrated in FIG. 9E, the second gate electrode 474 is connected to the first gate electrode 420 via the gate connection unit 475 that extends through the interlayer insulating layer 460. Accordingly, a voltage applied to the first gate electrode 420 is also applied to the second gate electrode 474, and an electric field is applied to the second semiconductor pattern 443. Because the second semiconductor pattern 443 is formed of the same or substantially the same material as that used to form the first semiconductor pattern 441, characteristics of the second semiconductor pattern 443 may be changed by light. The second gate electrode 474 blocks light emitted from above from reaching the second semiconductor pattern 443, and the first gate electrode 420 blocks light reflected by the lower surface of the substrate 410 from reaching the second semiconductor pattern 443. Accordingly, the second semiconductor pattern 443 of the thin film transistor TFT may have constant characteristics regardless of an ambient optical state.

As shown in FIG. 9E, the upper surface light barrier unit 471 is electrically connected to a bias line BL extending in a column direction. The bias line BL may be a portion of the third conductive layer 470 and thus may be integrally formed with the upper surface light barrier unit 471. Although the bias line BL extends in a column direction in FIG. 9E, this is only an example, and bias line BL may extend in a row direction and may be electrically connected to the upper surface light barrier units 471 of unit pixels PX arranged in a row direction. The bias line BL may be connected to the power unit 350 and may thus be supplied with the bias voltage Vb. The bias voltage Vb may be applied to the first electrode 451 via the upper surface light barrier unit 471 and the contact unit 472. The photosensitive thin film device PSD outputs the magnitude of a current flowing between the first electrode 451 and the second electrode 452 to the thin film transistor TFT according to the amount of light radiated onto the first semiconductor pattern 441. The thin film transistor TFT outputs the current via the output line OL in response to a gate signal applied to the first gate electrode 420.

Figure 10:
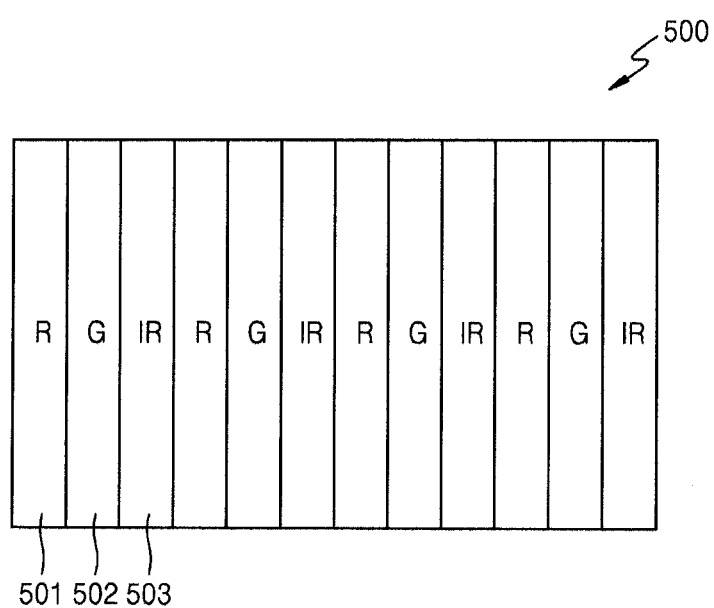
FIG. 10 is a plan view of a light-emission unit of a biometric information sensing apparatus, according to an embodiment of the present invention.

FIG. 10 is a plan view of a light-emission unit of a biometric information sensing apparatus, according to an embodiment of the present invention.

Referring to FIG. 10, a light-emission unit 500 may include a plurality of first light-emitting devices 501 for emitting red visible light, a plurality of second light-emitting devices 502 for emitting green visible light, and a plurality of third light-emitting devices 503 for emitting near-infrared light. The light-emission unit 500 may correspond to the light-emission unit 232 of FIG. 5.

Each of the first through third light-emitting devices 501, 502, and 503 may include an LED, an OLED, or an electroluminescence device.

Each of the first through third light-emitting devices 501, 502, and 503 may include a plurality of light-emitting devices arranged in a column direction. For example, a first light-emitting device 501 on the leftmost side of FIG. 10 may include red light-emitting devices that are controlled concurrently (e.g., simultaneously). The red light-emitting devices may be aligned in a column direction and may be commonly connected between a first line and a second line. A controller may control light emission of the red light-emitting devices by controlling a voltage of the first line. In the same way as described above, a second light-emitting device 502 may include green light-emitting devices controlled concurrently (e.g., simultaneously) and aligned in a column direction, and a third light-emitting device 503 may include infrared light-emitting devices controlled concurrently (e.g., simultaneously) and aligned in a column direction.

As shown in FIG. 10, the first light-emitting devices 501, the second light-emitting devices 502, and the third light-emitting devices 503 are arranged in a row direction. However, this is only an example. The red light-emitting devices, the green light-emitting devices, and the infrared light-emitting devices may be arranged in a matrix form.

Although the light-emission unit 500 includes the plurality of first light-emitting devices 501 for emitting red visible light, the plurality of second light-emitting devices 502 for emitting green visible light, and the plurality of third light-emitting devices 503 for emitting near-infrared light in FIG. 10, the light-emission unit 500 may include only the plurality of first light-emitting devices 501 for emitting red visible light, may include only the plurality of second light-emitting devices 502 for emitting green visible light, or may include only the plurality of third light-emitting devices 503 for emitting near-infrared light, according to application products. The light-emission unit 500 may further include light-emitting devices emitting blue visible light. Alternatively, the light-emission unit 500 may include only two types of light-emitting devices from among the first through third light-emitting devices 501, 502, and 503.

Figure 11:
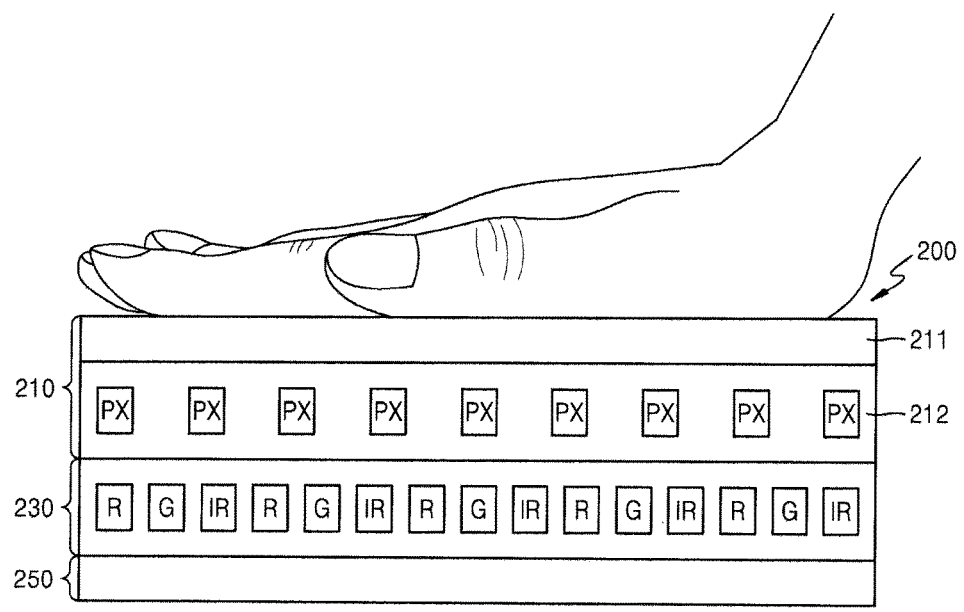
FIG. 11 illustrates a structure for sensing biometric information by using the biometric information sensing apparatus of FIG. 5.

FIG. 11 illustrates a structure for sensing biometric information by using the biometric information sensing apparatus 200 of FIG. 5.

Referring to FIG. 11, the biometric information sensing apparatus 200 includes a sensing unit 210, a light source unit 230, and a protection layer 250. The sensing unit 210 includes the first substrate 211 and the light sensor array 212. The light source unit 230 includes a plurality of first light-emitting devices R for emitting red visible light, a plurality of second light-emitting devices G for emitting green visible light, and a plurality of third light-emitting devices IR for emitting near-infrared light. The protection layer 250 protects the light source unit 230 and the sensing unit 210 from the outside. The protection layer 250 may be formed of a material that reflects light so that light emitted from the light source unit 230 is directed toward the sensing unit 210.

A portion (for example, a hand) of a body of which biometric information is to be sensed may be located on the first substrate 211. The light emitted from the light source unit 230 is radiated to the hand via the sensing unit 210. Light is reflected by veins, blood vessels, and/or the like within the hand, and the sensing unit 210 senses the reflected light.

The biometric information sensing apparatus 200 may sense veins existing in the hand of a human. Veins are arranged differently for different people. Accordingly, a pattern in which veins are arranged may be referred to as a vein pattern, and a human (e.g., a specific human) may be identified via this vein pattern. The vein pattern is attracting attention as authentication means, in addition to a fingerprint and/or an iris. A vein pattern is body information unique to a specific person and does not leave any trace, like a fingerprint that can be pressed onto an object, and thus a vein pattern has no risk of being stolen. The thickness or size of a vein may vary according to the growth of a person, but the person's vein pattern does not vary.

Oxyhemoglobin, including oxygen, flows in arteries, but deoxygenated hemoglobin, having reduced oxygen, flows in veins. The reduced hemoglobin absorbs light having a wavelength of about 760 nm, namely, near-infrared light. Accordingly, when only the third light-emitting devices IR of the light source unit 230 emit light and the sensing unit 210 senses the emitted light, a portion of the sensing unit 210 on which veins are positioned senses a smaller amount of near-infrared light than the other portions thereof. By using this property, the biometric information sensing apparatus 200 may sense a vein pattern of a user.

The biometric information sensing apparatus 200 may sense a pulse wave and a heart rate. The thicknesses and blood flows of arteries vary depending on a heartbeat. Arteries have the smallest thicknesses right before a left ventricle starts shrinking. When shrinkage of the left ventricle is maximized, the arteries have the largest thicknesses. Blood absorbs green light. Thus, the biometric information sensing apparatus 200 may sense a pulse wave by using green light. When only the second light-emitting devices G of the light source unit 230 emit light and the sensing unit 210 senses the emitted light, the amount of green light received varies according to a blood flow. By using this property, the biometric information sensing apparatus 200 may sense a blood flow. A blood flow that varies according to time corresponds to a pulse wave.

When the biometric information sensing apparatus 200 analyzes this pulse wave, the biometric information sensing apparatus 200 may sense a heart rate. The heart rate may correspond to a result of dividing 60 by a period (seconds) of the pulse wave. The period of the pulse wave may be sensed via the period of a time point when a blood flow is at a maximum, namely, a time point when the left ventricle maximally shrinks. When blood flow is at a maximum, a maximum of green light is absorbed by blood, and thus the sensing unit 210 may sense a smallest amount of green light.

The biometric information sensing apparatus 200 may sense oxygen saturation. The oxygen saturation represents a percentage of hemoglobin bonding with oxygen in red blood cells. Oxyhemoglobin, to which oxygen binds, and deoxygenated hemoglobin, from which oxygen is discharged, have different light-absorption spectra. Infrared light (for example, light having a wavelength of 900 nm) is constantly absorbed regardless of a ratio between oxyhemoglobin and deoxygenated hemoglobin. However, the higher a percentage of deoxygenated hemoglobin is, the larger an absorption rate of red light (for example, light having a wavelength of 665 nm). Thus, the biometric information sensing apparatus 200 may sense oxygen saturation by comparing a result of the sensing by the sensing unit 210 when only the third light-emitting devices IR of the light source unit 230 emit light with a result of the sensing by the sensing unit 210 when only the first light-emitting devices R of the light source unit 230 emit light.

As such, the biometric information sensing apparatus 200 may have, for example, three operation modes. In a first operation mode, which is a vein pattern sensing mode, the result of the sensing by the sensing unit 210 when only the third light-emitting devices IR of the light source unit 230 emit light may be used. In a second operation mode, which is a pulse wave and heart rate measuring mode, a result of the sensing by the sensing unit 210 when only the second light-emitting devices G of the light source unit 230 emit light may be used. In a third operation mode, which is an oxygen saturation measuring mode, a result of the sensing by the sensing unit 210 when the first light-emitting devices R and the third light-emitting devices IR alternately emit light may be used.

Figure 12:
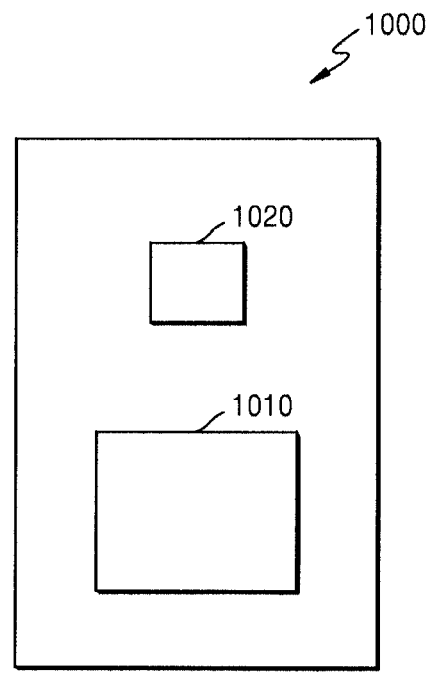
FIG. 12 is a block diagram of an apparatus including the biometric information sensing apparatus of FIG. 5.

FIG. 12 is a block diagram of an apparatus including the biometric information sensing apparatus 200 of FIG. 5.

Referring to FIG. 12, an apparatus 1000 may include a biometric information sensing apparatus 1010 and a controller 1020 for controlling the biometric information sensing apparatus 1010. The biometric information sensing apparatus 1010 may correspond to the biometric information sensing apparatus 200 of FIG. 5. The controller 1020 may be a microcontroller. The controller 1020 may include the timing controller 340 of FIG. 6 or may control the timing controller 340 of FIG. 6. The controller 1020 may receive image data from the timing controller 340 of FIG. 6, analyze the image data, and output an analysis result corresponding to each operation mode.

The controller 1020 may control the light-emission unit 232 of FIG. 5 or the light-emission unit 500 of FIG. 10. The controller 1020 may control only some of the light-emitting devices included in the light-emission unit 232 to emit light, according to operation modes.

The controller 1020 may determine an operation mode of the biometric information sensing apparatus 1010. The controller 1020 may control only some of the light-emitting devices included in the light-emission unit 500 to emit light, according to operation modes. For example, in the vein pattern sensing mode, the controller 1020 may control only the third light-emitting devices 503 to emit light. For example, in the pulse wave and heart rate measuring mode, the controller 1020 may control only the second light-emitting devices 502 to emit light. For example, in the oxygen saturation measuring mode, the controller 1020 may control the first light-emitting devices 501 and the third light-emitting devices 503 to alternately emit light.

The controller 1020 may receive image data acquired from the light sensor array 212 from the timing controller 340 when some of the light-emitting devices included in the light-emission unit 500 emit light according to operation modes, may analyze the received image data, and may output an analysis result corresponding to each operation mode.

The apparatus 1000 may be a portable terminal having a wireless communication function. The controller 1020 may have a wireless communication function. In this case, because a display device is disposed on a front surface of the apparatus 1000, the biometric information sensing apparatus 1010 may be disposed on a rear surface of the apparatus 1000. When a user holds the portable terminal 1000, the biometric information sensing apparatus 1010 contacts a hand of the user.

The controller 1020 may sense a vein pattern in the palm of the user by using the biometric information sensing apparatus 1010. The controller 1020 may previously store a vein pattern of an authorized user, and the controller 1020 may determine whether a user holding the portable terminal 1000 is the authorized user by comparing a vein pattern of the user acquired by the biometric information sensing apparatus 1010 with the pre-stored vein pattern.

The controller 1020 may sequentially operate in a plurality of operation modes. In a pulse wave and heart rate measuring mode, the biometric information sensing apparatus 1010 may measure the pulse wave and heart rate of the user. In an oxygen saturation measuring mode, the biometric information sensing apparatus 1010 may measure the oxygen saturation of the user. In a vein pattern sensing mode, the biometric information sensing apparatus 1010 may sense the vein pattern of the user. Because the pulse wave, heart rate, and oxygen saturation of the user are personal information, measured values thereof should not be open to the public. Based on the sensed vein pattern, the controller 1020 may match the measured pulse wave, heart rate, or oxygen saturation as body information with the user and store the body information matched with the user. When the controller 1020 operates in the vein pattern sensing mode and senses the vein pattern of the user, the controller 1020 may provide stored body information only to the user having the sensed vein pattern.

Figure 13:
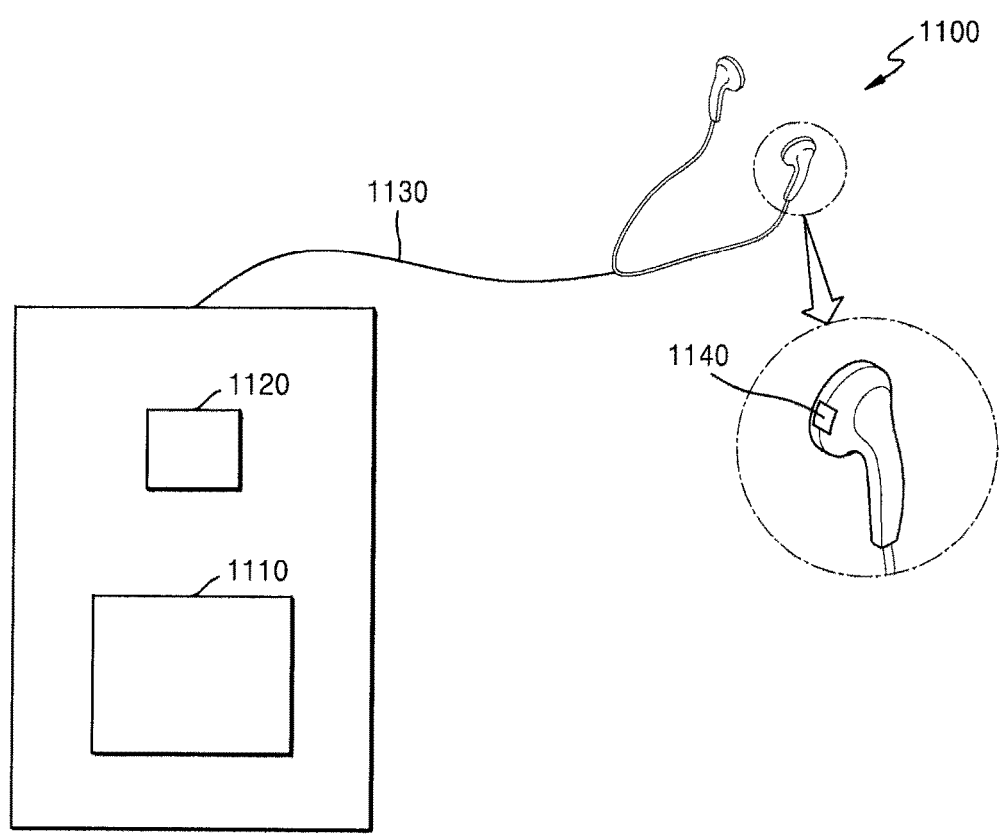
FIG. 13 illustrates another apparatus including the biometric information sensing apparatus of FIG. 5.

FIG. 13 illustrates another apparatus including the biometric information sensing apparatus 200 of FIG. 5.

Referring to FIG. 13, an apparatus 1100 may include a biometric information sensing apparatus 1110 and a controller 1120 for controlling the biometric information sensing apparatus 1110. The biometric information sensing apparatus 1110 and the controller 1120 may correspond to the biometric information sensing apparatus 1010 and the controller 1020 of FIG. 12, and repeated descriptions thereof may be omitted. The description below will focus on the differences therebetween. The biometric information sensing apparatus 1110 will be described later in more detail with reference to FIG. 14.

An earphone 1130 may be connected to the apparatus 1100. Electrodes 1140 may be disposed on both speaker portions of the earphone 1130, respectively. When the speaker portions of the earphone 1130 are inserted into the ears of a user, the electrodes 1140 directly contact the ears of the user. The controller 1120 may measure an electrocardiogram of the user by using the two electrodes 1140 disposed on the earphone 1130.

Figure 14:
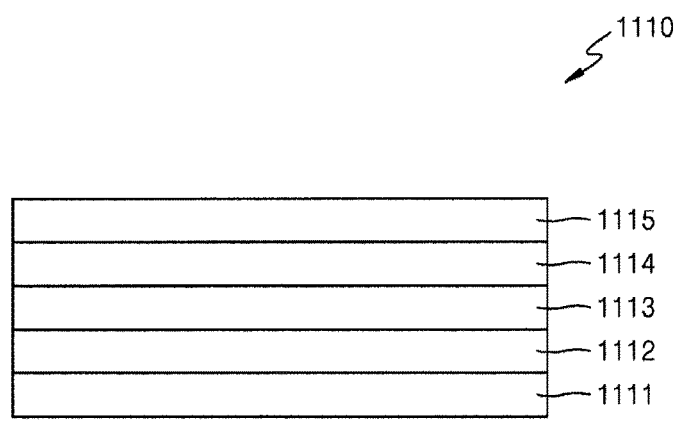
FIG. 14 is a schematic block diagram of the biometric information sensing apparatus of FIG. 13.

FIG. 14 is a schematic block diagram of the biometric information sensing apparatus 1110 of FIG. 13.

Referring to FIG. 14, the biometric information sensing apparatus 1110 includes a protection layer 1111, a light source unit 1112 (e.g., a light source 1112), a light sensor array 1113, a substrate 1114, and a transparent electrode 1115. The protection layer 1111, the light source unit 1112, the light sensor array 1113, and the substrate 1114 may correspond to the protection layer 250, the light source unit 230, the light sensor array 212, and the first substrate 211 of FIG. 11, respectively. Repeated descriptions thereof may be omitted herein. The transparent electrode 1115 is disposed on the substrate 1114, and a body contacts the transparent electrode 1115. The transparent electrode 1115 may transmit light emitted from the light source unit 1112, and transmits light reflected by the body so that the reflected light reaches the light sensor array 1113. The transparent electrode 1115 may be connected to the controller 1120 of FIG. 13.

Referring back to FIG. 13, the controller 1120 may measure the electrocardiogram of the user holding the apparatus 1100 with his or her hand, by using the transparent electrode 1115 of the biometric information sensing apparatus 1110, and the two electrodes 1140 of the earphone 1130.

Because both ears and a palm of the user contact the electrodes 1140 and the transparent electrode 1115, the controller 1120 may measure the electrocardiogram of the user by using the electrodes 1140 and the transparent electrode 1115. Electrocardiogram means an electrical activity of the heart.

When a user holds the apparatus 1100, the palm of the user contacts the biometric information sensing apparatus 1110.

The controller 1120 may sense the vein pattern of the user in the vein pattern sensing mode by using the biometric information sensing apparatus 1110. The controller 1120 may also measure the electrocardiogram of the user by using the two electrodes 1140 and the transparent electrode 1115. Electrocardiogram information is personal body information of a user and thus corresponds to information that requires security. When the controller 1120 measures the electrocardiogram, the controller 1120 may sense the vein pattern of the user by using the biometric information sensing apparatus 1110 and may store the vein pattern of the user together with an electrocardiogram result. Then, the controller 1120 may operate in a vein pattern sensing mode and may sense the vein pattern of the user and provide only a user having an identical vein pattern (e.g., a same vein pattern) with the sensed vein pattern with his or her electrocardiogram information.

Figure 15:
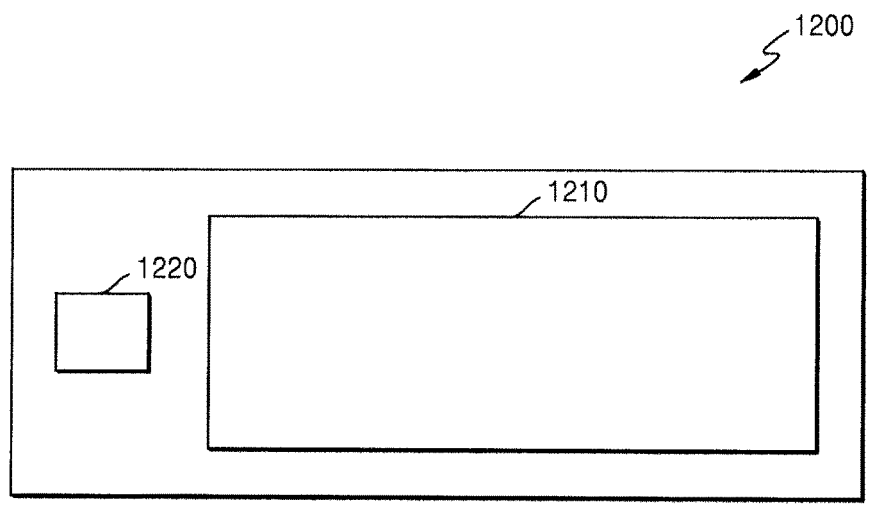
FIG. 15 is a block diagram of an apparatus including the biometric information sensing apparatus of FIG. 5.

FIG. 15 is a block diagram of an apparatus including the biometric information sensing apparatus 200 of FIG. 5.

Referring to FIG. 15, an apparatus 1200 may include a biometric information sensing apparatus 1210 and a controller 1220 for controlling the biometric information sensing apparatus 1210. The biometric information sensing apparatus 1210 may correspond to the biometric information sensing apparatus 200 of FIG. 5. The controller 1220 may be a microcontroller. The controller 1220 may include the timing controller 340 of FIG. 6 or may control the timing controller 340 of FIG. 6. The controller 1220 may receive image data from the timing controller 340 of FIG. 6, analyze the image data, and output an analysis result corresponding to each operation mode. The biometric information sensing apparatus 1210 and the controller 1220 may correspond to the biometric information sensing apparatus 1010 and the controller 1020 of FIG. 12, respectively.

The first and second substrates 211 and 231 of the biometric information sensing apparatus 1210 may be formed of a flexible material. Accordingly, the apparatus 1200 may also be bendable, foldable, or rollable. For example, the apparatus 1200 may be wound around the wrist of a user. The apparatus 1200 may be wound around the wrist of a user and may precisely sense the vein pattern of the wrist or measure a pulse wave and a heart rate from arteries flowing in the wrist and measure oxygen saturation.

The apparatus 1200 may further include a fixing member, such as a hook and loop fastener (e.g., Velcro®), so that the apparatus 1200 may be wound around the wrist and fixed to the wrist. Velcro® is a registered trademark of Velcro industries B.V. LIMITED LIABILITY COMPANY NETHERLANDS, Castorweg, 22-24 Curacao, NETHERLANDS. The apparatus 1200 may be attached to, for example, a bottom surface of a general watch.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present invention as defined by the following claims and their equivalents.

What is claimed is:

1. A photosensitive thin film device comprising:
a substrate that is transparent and insulative;
a first electrode on the substrate;
a semiconductor layer on the substrate and surrounding a perimeter of the first electrode;
a second electrode on the substrate and surrounding a perimeter of the semiconductor layer;
an interlayer insulating layer on the semiconductor layer and the first and second electrodes and having a first aperture exposing the first electrode; and
a conductive layer comprising an upper surface light barrier arranged on the interlayer insulating layer and covering an upper surface of the semiconductor layer, and a contact plug extending from the upper surface light barrier and connected to the first electrode via the first aperture,
wherein the contact plug does not directly contact the semiconductor layer and the second electrode.

2. The photosensitive thin film device of claim 1,
wherein the semiconductor layer has a ring-type planar shape having an inner edge and an outer edge,
wherein the first electrode is arranged inside the inner edge and contacts the inner edge, and
wherein the second electrode contacts the outer edge.

3. The photosensitive thin film device of claim 1, wherein the semiconductor layer has a circular ring-type planar shape having a circular inner edge and a circular outer edge.

4. The photosensitive thin film device of claim 1, wherein the semiconductor layer comprises:
a first semiconductor layer on the substrate; and
second semiconductor layers arranged between the first semiconductor layer and the first and second electrodes, the second semiconductor layers comprising heavily-doped impurities.

5. The photosensitive thin film device of claim 1,
wherein the interlayer insulating layer has a second aperture spaced apart from the second electrode and surrounding a portion of a perimeter of the second electrode, and
wherein the conductive layer further comprises a lateral surface light barrier extending from the upper surface light barrier along the second aperture and covering a portion of a lateral surface of the semiconductor layer in a lateral direction.

6. The photosensitive thin film device of claim 5, further comprising a connection line that extends from the second electrode in a lateral direction via a hole in the lateral surface light barrier on the substrate, the connection line being insulated from the lateral surface light barrier by the interlayer insulating layer.

7. The photosensitive thin film device of claim 6, wherein the upper and lateral surface light barriers of the conductive layer are configured to block light radiated from above the conductive layer toward the substrate from reaching the semiconductor layer.

8. The photosensitive thin film device of claim 1, wherein as an amount of light radiated from below the substrate onto the semiconductor layer increases, a magnitude of a current flowing between the first and second electrodes via the semiconductor layer increases.

9. A biometric information sensing apparatus comprising:
a substrate that is transparent and insulative;
a light sensor array comprising a plurality of pixels arranged in a matrix form on the substrate, each of the pixels comprising a photosensitive thin film device; and
a light-emission unit arranged on the light sensor array and configured to emit light,
wherein the photosensitive thin film device comprises:
a first semiconductor pattern of a ring type having an inner edge and an outer edge, the first semiconductor pattern being on the substrate;
a first electrode arranged inside the inner edge on the substrate and connected to the first semiconductor pattern;
a second electrode surrounding a perimeter of the first semiconductor pattern along the outer edge;
an interlayer insulating layer arranged on the first semiconductor pattern and the first and second electrodes and having a first aperture exposing the first electrode; and
a light barrier electrode comprising an upper surface light barrier arranged on the interlayer insulating layer and covering an upper surface of the first semiconductor pattern, and a contact plug extending from the upper surface light barrier and connected to the first electrode via the first aperture.

10. The biometric information sensing apparatus of claim 9, wherein the light-emission unit comprises at least one of a first light-emitting device configured to emit visible light of a first color, a second light-emitting device configured to emit visible light of a second color, and a third light-emitting device configured to emit near-infrared light.

11. The biometric information sensing apparatus of claim 9,
wherein each of the plurality of pixels comprises a thin film transistor, and
wherein the thin film transistor comprises:
a second semiconductor pattern on the substrate, the second semiconductor pattern having first and second impurity regions and a channel region between the first and second impurity regions;
a first gate electrode between the substrate and the second semiconductor pattern such that at least a portion of the first gate electrode overlaps the channel region;
a third electrode connected to the first impurity region; and
a fourth electrode connected to the second impurity region and the second electrode of the photosensitive thin film device.

12. The biometric information sensing apparatus of claim 11, wherein the thin film transistor further comprises a second gate electrode connected to the first gate electrode via a contact plug that extends through the interlayer insulating layer, the second gate electrode being arranged on the interlayer insulating layer such that at least a portion of the second gate electrode overlaps the channel region.

13. The biometric information sensing apparatus of claim 11, wherein the light sensor array further comprises:
gate lines that electrically connect the first gate electrodes of the thin film transistors of pixels on a same row from among the plurality of pixels to one another;
output lines that electrically connect the third electrodes of the thin film transistors of pixels on a same column from among the plurality of pixels to one another; and a bias line that electrically connects the light barrier electrodes of the photosensitive thin film devices of the plurality of pixels to one another.

14. The biometric information sensing apparatus of claim 13, further comprising:
   a power supply configured to apply a bias voltage to the bias line; and
   an image sensor controller configured to sequentially drive the gate lines, receive sensing signals output from the plurality of pixels via the output lines, and generate image data based on the sensing signals.

15. The biometric information sensing apparatus of claim 14, wherein the light-emission unit comprises a plurality of first light-emitting devices configured to emit red visible light, a plurality of second light-emitting devices configured to emit green visible light, and a plurality of third light-emitting devices configured to emit near-infrared light.

16. The biometric information sensing apparatus of claim 15, further comprising a controller configured to control at least one of the first light-emitting devices, the second light-emitting devices, and the third light-emitting devices to emit light according to operation modes, receive image data from the image sensor controller, and analyze the image data according to the operation modes.

17. The biometric information sensing apparatus of claim 16, wherein the controller is configured to control the third light-emitting devices to emit light in a vein pattern sensing mode, control the second light-emitting devices to emit light in a pulse wave sensing mode or a heart rate measuring mode, and control the first light-emitting devices and the third light-emitting devices to alternately emit light in an oxygen saturation measuring mode.

18. The biometric information sensing apparatus of claim 17, wherein the biometric information sensing apparatus comprises a portable terminal having a wireless communication function.

19. The biometric information sensing apparatus of claim 18, wherein the controller is configured to authenticate a user by comparing a vein pattern of the user acquired by analyzing the image data in the vein pattern sensing mode with a pre-stored vein pattern.

20. The biometric information sensing apparatus of claim 19, further comprising:
   a transparent electrode arranged below the substrate; and
   earphones configured to be connected to the portable terminal and comprising first and second electrocardiogram sensing electrodes that respectively contact both ears of the user,
   wherein the controller measures an electrocardiogram of the user via the first and second electrocardiogram sensing electrodes and the transparent electrode.

* * * * *